(12) United States Patent
Dajani et al.

(10) Patent No.: US 10,479,698 B2
(45) Date of Patent: Nov. 19, 2019

(54) SYSTEM AND METHOD FOR AN AUTOMATED WATER TESTING DEVICE

(71) Applicants: Mohamad Tarek Dajani, Beirut (LB); Rabih Krayem, Bauchrieh (LB); Jad Berro, Beirut (LB); Michael Chaftari, Beirut (LB)

(72) Inventors: Mohamad Tarek Dajani, Beirut (LB); Rabih Krayem, Bauchrieh (LB); Jad Berro, Beirut (LB); Michael Chaftari, Beirut (LB)

(*) Notice: Subject to any disclaimer, the term of this patent is extended or adjusted under 35 U.S.C. 154(b) by 251 days.

(21) Appl. No.: 15/643,781

(22) Filed: Jul. 7, 2017

(65) Prior Publication Data
US 2018/0118579 A1 May 3, 2018

Related U.S. Application Data

(60) Provisional application No. 62/415,473, filed on Oct. 31, 2016.

(51) Int. Cl.
*G01N 1/10* (2006.01)
*C02F 1/00* (2006.01)
*G01N 1/44* (2006.01)
*G01N 33/18* (2006.01)

(52) U.S. Cl.
CPC ........... *C02F 1/008* (2013.01); *G01N 1/10* (2013.01); *G01N 1/44* (2013.01); *G01N 33/1813* (2013.01); *C02F 1/00* (2013.01); *C02F 2209/29* (2013.01)

(58) Field of Classification Search
USPC ............... 436/165, 172; 422/68.1, 400–402; 73/1.01–1.02, 53.01
See application file for complete search history.

(56) References Cited

U.S. PATENT DOCUMENTS

| | | | |
|---|---|---|---|
| 7,360,402 B2 | 4/2008 | Liao | |
| 8,065,906 B2* | 11/2011 | Wiese | G01N 31/16 210/749 |
| 9,012,234 B2* | 4/2015 | Lundgreen | G01N 33/1886 436/165 |
| 2005/0276724 A1* | 12/2005 | Bremauer | B01F 15/0217 422/29 |
| 2007/0178010 A1* | 8/2007 | Connelly | G01N 1/14 422/68.1 |
| 2015/0235545 A1 | 8/2015 | Schoenheit et al. | |

* cited by examiner

*Primary Examiner* — Nina Bhat

(57) ABSTRACT

A system and method includes receiving at least one instruction from a first computing system to schedule a test of a fluid. An input device is operated for importing at least a quantity of the fluid from a source. A filling device is instructed for filling a vial with a pre-determined amount of the imported fluid. A drawing device is operated for drawing a pre-determined amount of a reagent. The drawing device is activated for adding the pre-determined amount of the reagent to the vial. An output of a photocolorimeter is read. The output indicates a reaction of the pre-determined amount of the imported fluid and the pre-determined amount of the reagent. A result of the test is transmitted to a second computing system.

11 Claims, 9 Drawing Sheets

SYSTEM AND METHOD FOR AN AUTOMATED WATER TESTING DEVICE

CROSS-REFERENCE TO RELATED APPLICATIONS

The present Utility patent application claims priority benefit of the U.S. provisional application for patent Ser. No. 62/415,473 entitled "REEF BOT", filed on 31 Oct. 2016 under 35 U.S.C. 119(e). The contents of this related provisional application are incorporated herein by reference for all purposes to the extent that such subject matter is not inconsistent herewith or limiting hereof.

RELATED CO-PENDING U.S. PATENT APPLICATIONS

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection by the author thereof. The copyright owner has no objection to the facsimile reproduction by anyone of the patent document or patent disclosure for the purposes of referencing as patent prior art, as it appears in the Patent and Trademark Office, patent file or records, but otherwise reserves all copyright rights whatsoever.

BACKGROUND OF THE RELEVANT PRIOR ART

One or more embodiments of the invention generally relate to an automated device for testing water. More particularly, certain embodiments of the invention relate to an automated colorimetric and titrimetric device for testing water.

Various methods are used in the industry for testing of water. Typically, there are statutory requirements for the quality of water required for various uses. Accordingly, water may be tested for its potability (human consumption) i.e., for drinking, cooking, etc. . . . or for its usability i.e., for use in swimming pools, aquariums, bathing, chemical reactions, cleaning, etc. . . . . . Generally water may be tested for suspended matter, dissolved matter, pH, etc. . . . . . The quality of water used for these various purposes varies. The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, another aspect of the prior art generally useful to be aware of is that manual techniques may be used for a major portion of water testing. Specific devices may be available for specific uses like determining the quality of aquarium water, swimming pool water, etc. . . . . . One can expect that the failure of the manual testing since it may lead to inaccurate results due to manual error. The devices too may not have the versatility to test water from multiple sources simultaneously.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
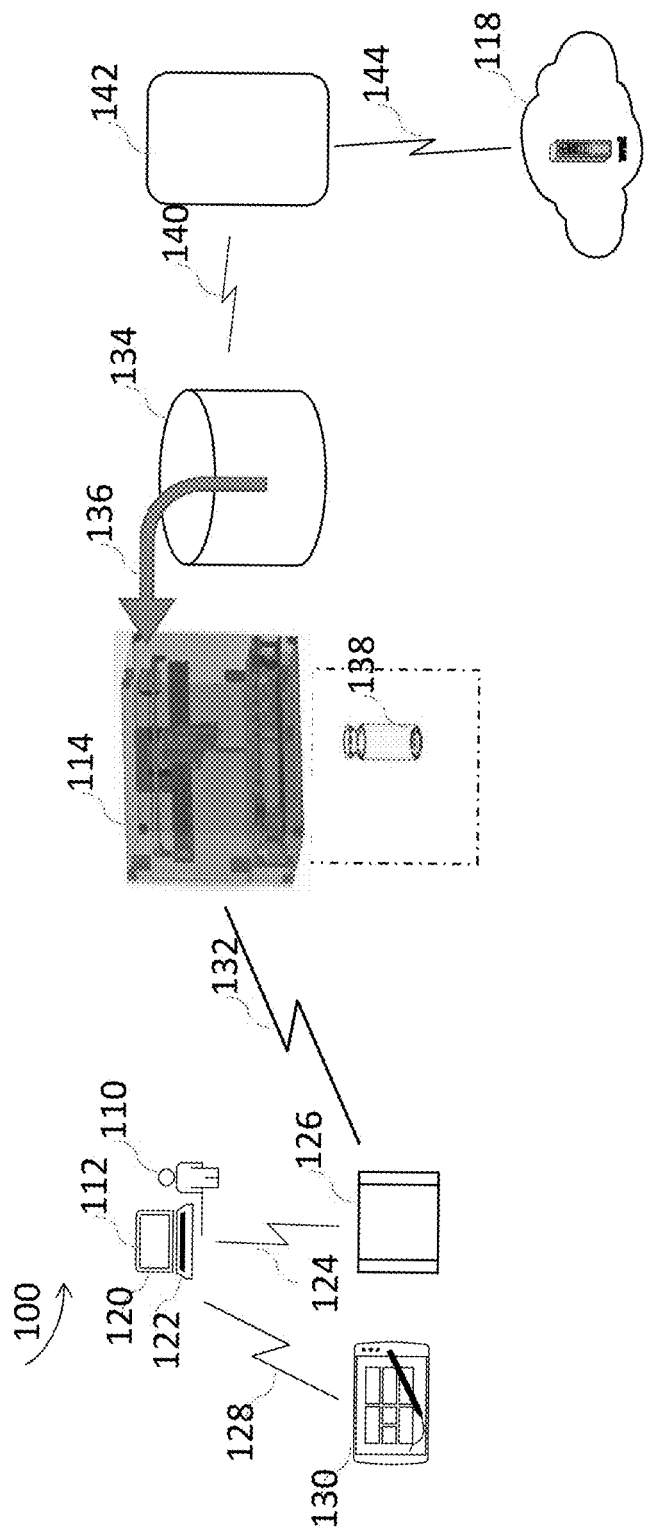
FIG. 1 illustrates an exemplary system for testing water, in accordance with an embodiment of the present invention.

Unless otherwise indicated illustrations in the figures are not necessarily drawn to scale.

DETAILED DESCRIPTION OF SOME EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

All words of approximation as used in the present disclosure and claims should be construed to mean "approximate," rather than "perfect," and may accordingly be employed as a meaningful modifier to any other word, specified parameter, quantity, quality, or concept. Words of approximation, include, yet are not limited to terms such as "substantial", "nearly", "almost", "about", "generally", "largely", "essentially", "closely approximate", etc.

As will be established in some detail below, it is well settle law, as early as 1939, that words of approximation are not indefinite in the claims even when such limits are not defined or specified in the specification.

For example, see Ex parte Mallory, 52 USPQ 297, 297 (Pat. Off. Bd. App. 1941) where the court said "The examiner has held that most of the claims are inaccurate because apparently the laminar film will not be entirely eliminated. The claims specify that the film is "substantially" eliminated and for the intended purpose, it is believed that the slight portion of the film which may remain is negligible. We are of the view, therefore, that the claims may be regarded as sufficiently accurate."

Note that claims need only "reasonably apprise those skilled in the art" as to their scope to satisfy the definiteness requirement. See Energy Absorption Sys., Inc. v. Roadway Safety Servs., Inc., Civ. App. 96-1264, slip op. at 10 (Fed. Cir. Jul. 3, 1997) (unpublished) Hybridtech v. Monoclonal Antibodies, Inc., 802 F.2d 1367, 1385, 231 USPQ 81, 94 (Fed. Cir. 1986), cert. denied, 480 U.S. 947 (1987). In addition, the use of modifiers in the claim, like "generally" and "substantial," does not by itself render the claims indefinite. See Seattle Box Co. v. Industrial Crating & Packing, Inc., 731 F.2d 818, 828-29, 221 USPQ 568, 575-76 (Fed. Cir. 1984).

Moreover, the ordinary and customary meaning of terms like "substantially" includes "reasonably close to: nearly, almost, about", connoting a term of approximation. See In re Frye, Appeal No. 2009-006013, 94 USPQ2d 1072, 1077, 2010 WL 889747 (B.P.A.I. 2010) Depending on its usage, the word "substantially" can denote either language of approximation or language of magnitude. Deering Precision Instruments, L.L.C. v. Vector Distribution Sys., Inc., 347 F.3d 1314, 1323 (Fed. Cir. 2003) (recognizing the "dual ordinary meaning of th[e] term ["substantially"] as connoting a term of approximation or a term of magnitude"). Here, when referring to the "substantially halfway" limitation, the Specification uses the word "approximately" as a substitute for the word "substantially" (Fact 4). (Fact 4). The ordinary meaning of "substantially halfway" is thus reasonably close to or nearly at the midpoint between the forwardmost point of the upper or outsole and the rearwardmost point of the upper or outsole.

Similarly, the term 'substantially' is well recognize in case law to have the dual ordinary meaning of connoting a term of approximation or a term of magnitude. See Dana Corp. v. American Axle & Manufacturing, Inc., Civ. App. 04-1116, 2004 U.S. App. LEXIS 18265, *13-14 (Fed. Cir. Aug. 27, 2004) (unpublished). The term "substantially" is commonly used by claim drafters to indicate approximation. See Cordis Corp. v. Medtronic AVE Inc., 339 F.3d 1352, 1360 (Fed. Cir. 2003) ("The patents do not set out any numerical standard by which to determine whether the thickness of the wall surface is 'substantially uniform.' The term 'substantially,' as used in this context, denotes approximation. Thus, the walls must be of largely or approximately uniform thickness."); see also Deering Precision Instruments, LLC v. Vector Distribution Sys., Inc., 347 F.3d 1314, 1322 (Fed. Cir. 2003); Epcon Gas Sys., Inc. v. Bauer Compressors, Inc., 279 F.3d 1022, 1031 (Fed. Cir. 2002). We find that the term "substantially" was used in just such a manner in the claims of the patents-in-suit: "substantially uniform wall thickness" denotes a wall thickness with approximate uniformity.

It should also be noted that such words of approximation as contemplated in the foregoing clearly limits the scope of claims such as saying 'generally parallel' such that the adverb 'generally' does not broaden the meaning of parallel. Accordingly, it is well settled that such words of approximation as contemplated in the foregoing (e.g., like the phrase 'generally parallel') envisions some amount of deviation from perfection (e.g., not exactly parallel), and that such words of approximation as contemplated in the foregoing are descriptive terms commonly used in patent claims to avoid a strict numerical boundary to the specified parameter. To the extent that the plain language of the claims relying on such words of approximation as contemplated in the foregoing are clear and uncontradicted by anything in the written description herein or the figures thereof, it is improper to rely upon the present written description, the figures, or the prosecution history to add limitations to any of the claim of the present invention with respect to such words of approximation as contemplated in the foregoing. That is, under such circumstances, relying on the written description and prosecution history to reject the ordinary and customary meanings of the words themselves is impermissible. See, for example, Liquid Dynamics Corp. v. Vaughan Co., 355 F.3d 1361, 69 USPQ2d 1595, 1600-01 (Fed. Cir. 2004). The plain language of phrase 2 requires a "substantial helical flow." The term "substantial" is a meaningful modifier implying "approximate," rather than "perfect." In Cordis Corp. v. Medtronic AVE, Inc., 339 F.3d 1352, 1361 (Fed. Cir. 2003), the district court imposed a precise numeric constraint on the term "substantially uniform thickness." We noted that the proper interpretation of this term was "of largely or approximately uniform thickness" unless something in the prosecution history imposed the "clear and unmistakable disclaimer" needed for narrowing beyond this simple-language interpretation. Id. In Anchor Wall Systems v. Rockwood Retaining Walls, Inc., 340 F.3d 1298, 1311 (Fed. Cir. 2003)" Id. at 1311. Similarly, the plain language of claim 1 requires neither a perfectly helical flow nor a flow that returns precisely to the center after one rotation (a limitation that arises only as a logical consequence of requiring a perfectly helical flow).

The reader should appreciate that case law generally recognizes a dual ordinary meaning of such words of approximation, as contemplated in the foregoing, as connoting a term of approximation or a term of magnitude; e.g., see Deering Precision Instruments, L.L.C. v. Vector Distrib. Sys., Inc., 347 F.3d 1314, 68 USPQ2d 1716, 1721 (Fed. Cir. 2003), cert. denied, 124 S. Ct. 1426 (2004) where the court was asked to construe the meaning of the term "substantially" in a patent claim. Also see Epcon, 279 F.3d at 1031 ("The phrase 'substantially constant' denotes language of approximation, while the phrase 'substantially below' signifies language of magnitude, i.e., not insubstantial."). Also, see, e.g., Epcon Gas Sys., Inc. v. Bauer Compressors, Inc., 279 F.3d 1022 (Fed. Cir. 2002) (construing the terms "substantially constant" and "substantially below"); Zodiac Pool Care, Inc. v. Hoffinger Indus., Inc., 206 F.3d 1408 (Fed. Cir. 2000) (construing the term "substantially inward"); York Prods., Inc. v. Cent. Tractor Farm & Family Ctr., 99 F.3d 1568 (Fed. Cir. 1996) (construing the term "substantially the entire height thereof"); Tex. Instruments Inc. v. Cypress Semiconductor Corp., 90 F.3d 1558 (Fed. Cir. 1996) (construing the term "substantially in the common plane"). In conducting their analysis, the court instructed to begin with the ordinary meaning of the claim terms to one of ordinary skill in the art. Prima Tek, 318 F.3d at 1148. Reference to dictionaries and our cases indicates that the term "substantially" has numerous ordinary meanings. As the district court stated, "substantially" can mean "significantly" or "considerably." The term "substantially" can also mean "largely" or "essentially." Webster's New 20th Century Dictionary 1817 (1983).

Words of approximation, as contemplated in the foregoing, may also be used in phrases establishing approximate ranges or limits, where the end points are inclusive and approximate, not perfect; e.g., see AK Steel Corp. v. Sollac, 344 F.3d 1234, 68 USPQ2d 1280, 1285 (Fed. Cir. 2003) where it where the court said [W]e conclude that the ordinary meaning of the phrase "up to about 10%" includes the "about 10%" endpoint. As pointed out by AK Steel, when an object of the preposition "up to" is nonnumeric, the most natural meaning is to exclude the object (e.g., painting the wall up to the door). On the other hand, as pointed out by Sollac, when the object is a numerical limit, the normal meaning is to include that upper numerical limit (e.g., counting up to ten, seating capacity for up to seven passengers). Because we have here a numerical limit—"about 10%"—the ordinary meaning is that that endpoint is included.

In the present specification and claims, a goal of employment of such words of approximation, as contemplated in the foregoing, is to avoid a strict numerical boundary to the modified specified parameter, as sanctioned by Pall Corp. v. Micron Separations, Inc., 66 F.3d 1211, 1217, 36 USPQ2d 1225, 1229 (Fed. Cir. 1995) where it states "It is well established that when the term "substantially" serves reasonably to describe the subject matter so that its scope would be understood by persons in the field of the invention, and to distinguish the claimed subject matter from the prior art, it is not indefinite." Likewise see Verve LLC v. Crane Cams Inc., 311 F.3d 1116, 65 USPQ2d 1051, 1054 (Fed. Cir. 2002). Expressions such as "substantially" are used in patent documents when warranted by the nature of the invention, in order to accommodate the minor variations that may be appropriate to secure the invention. Such usage may well satisfy the charge to "particularly point out and distinctly claim" the invention, 35 U.S.C. § 112, and indeed may be necessary in order to provide the inventor with the benefit of his invention. In Andrew Corp. v. Gabriel Elecs. Inc., 847 F.2d 819, 821-22, 6 USPQ2d 2010, 2013 (Fed. Cir. 1988) the court explained that usages such as "substantially equal" and "closely approximate" may serve to describe the invention with precision appropriate to the technology and without intruding on the prior art. The court again explained in Ecolab Inc. v. Envirochem, Inc., 264 F.3d 1358, 1367, 60 USPQ2d 1173, 1179 (Fed. Cir. 2001) that "like the term 'about,' the term 'substantially' is a descriptive term commonly used in patent claims to 'avoid a strict numerical boundary to the specified parameter, see Ecolab Inc. v. Envirochem Inc., 264 F.3d 1358, 60 USPQ2d 1173, 1179 (Fed. Cir. 2001) where the court found that the use of the term "substantially" to modify the term "uniform" does not render this phrase so unclear such that there is no means by which to ascertain the claim scope.

Similarly, other courts have noted that like the term "about," the term "substantially" is a descriptive term commonly used in patent claims to "avoid a strict numerical boundary to the specified parameter."; e.g., see Pall Corp. v. Micron Seps., 66 F.3d 1211, 1217, 36 USPQ2d 1225, 1229 (Fed. Cir. 1995); see, e.g., Andrew Corp. v. Gabriel Elecs. Inc., 847 F.2d 819, 821-22, 6 USPQ2d 2010, 2013 (Fed. Cir. 1988) (noting that terms such as "approach each other," "close to," "substantially equal," and "closely approximate" are ubiquitously used in patent claims and that such usages, when serving reasonably to describe the claimed subject matter to those of skill in the field of the invention, and to distinguish the claimed subject matter from the prior art, have been accepted in patent examination and upheld by the courts). In this case, "substantially" avoids the strict 100% nonuniformity boundary.

Indeed, the foregoing sanctioning of such words of approximation, as contemplated in the foregoing, has been established as early as 1939, see Ex parte Mallory, 52 USPQ 297, 297 (Pat. Off. Bd. App. 1941) where, for example, the court said "the claims specify that the film is "substantially" eliminated and for the intended purpose, it is believed that the slight portion of the film which may remain is negligible. We are of the view, therefore, that the claims may be regarded as sufficiently accurate." Similarly, In re Hutchison, 104 F.2d 829, 42 USPQ 90, 93 (C.C.P.A. 1939) the court said "It is realized that "substantial distance" is a relative and somewhat indefinite term, or phrase, but terms and phrases of this character are not uncommon in patents in cases where, according to the art involved, the meaning can be determined with reasonable clearness."

Hence, for at least the forgoing reason, Applicants submit that it is improper for any examiner to hold as indefinite any claims of the present patent that employ any words of approximation.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will be described in detail below with reference to embodiments thereof as illustrated in the accompanying drawings.

References to a "device," an "apparatus," a "system," etc., in the preamble of a claim should be construed broadly to mean "any structure meeting the claim terms" exempt for any specific structure(s)/type(s) that has/(have) been explicitly disavowed or excluded or admitted/implied as prior art in the present specification or incapable of enabling an object/aspect/goal of the invention. Furthermore, where the present specification discloses an object, aspect, function, goal, result, or advantage of the invention that a specific prior art structure and/or method step is similarly capable of performing yet in a very different way, the present invention disclosure is intended to and shall also implicitly include and cover additional corresponding alternative embodiments that are otherwise identical to that explicitly disclosed except that they exclude such prior art structure(s)/step(s), and shall accordingly be deemed as providing sufficient disclosure to support a corresponding negative limitation in a claim claiming such alternative embodiment(s), which exclude such very different prior art structure(s)/step(s) way(s).

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," "some embodiments," "embodiments of the invention," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least some embodiments of the invention" includes the stated particular feature, structure, or characteristic.

References to "user", or any similar term, as used herein, may mean a human or non-human user thereof. Moreover, "user", or any similar term, as used herein, unless expressly stipulated otherwise, is contemplated to mean users at any stage of the usage process, to include, without limitation, direct user(s), intermediate user(s), indirect user(s), and end user(s). The meaning of "user", or any similar term, as used herein, should not be otherwise inferred or induced by any pattern(s) of description, embodiments, examples, or referenced prior-art that may (or may not) be provided in the present patent.

References to "end user", or any similar term, as used herein, is generally intended to mean late stage user(s) as opposed to early stage user(s). Hence, it is contemplated that there may be a multiplicity of different types of "end user" near the end stage of the usage process. Where applicable, especially with respect to distribution channels of embodiments of the invention comprising consumed retail products/services thereof (as opposed to sellers/vendors or Original Equipment Manufacturers), examples of an "end user" may include, without limitation, a "consumer", "buyer", "customer", "purchaser", "shopper", "enjoyer", "viewer", or individual person or non-human thing benefiting in any way, directly or indirectly, from use of. or interaction, with some aspect of the present invention.

In some situations, some embodiments of the present invention may provide beneficial usage to more than one stage or type of usage in the foregoing usage process. In such cases where multiple embodiments targeting various stages of the usage process are described, references to "end user", or any similar term, as used therein, are generally intended to not include the user that is the furthest removed, in the foregoing usage process, from the final user therein of an embodiment of the present invention.

Where applicable, especially with respect to retail distribution channels of embodiments of the invention, intermediate user(s) may include, without limitation, any individual person or non-human thing benefiting in any way, directly or indirectly, from use of, or interaction with, some aspect of the present invention with respect to selling, vending, Original Equipment Manufacturing, marketing, merchandising, distributing, service providing, and the like thereof.

References to "person", "individual", "human", "a party", "animal", "creature", or any similar term, as used herein, even if the context or particular embodiment implies living user, maker, or participant, it should be understood that such characterizations are sole by way of example, and not limitation, in that it is contemplated that any such usage, making, or participation by a living entity in connection with making, using, and/or participating, in any way, with embodiments of the present invention may be substituted by such similar performed by a suitably configured non-living entity, to include, without limitation, automated machines, robots, humanoids, computational systems, information processing systems, artificially intelligent systems, and the like. It is further contemplated that those skilled in the art will readily recognize the practical situations where such living makers, users, and/or participants with embodiments of the present invention may be in whole, or in part, replaced with such non-living makers, users, and/or participants with embodiments of the present invention. Likewise, when those skilled in the art identify such practical situations where such living makers, users, and/or participants with embodiments of the present invention may be in whole, or in part, replaced with such non-living makers, it will be readily apparent in light of the teachings of the present invention how to adapt the described embodiments to be suitable for such non-living makers, users, and/or participants with embodiments of the present invention. Thus, the invention is thus to also cover all such modifications, equivalents, and alternatives falling within the spirit and scope of such adaptations and modifications, at least in part, for such non-living entities.

Headings provided herein are for convenience and are not to be taken as limiting the disclosure in any way.

The enumerated listing of items does not imply that any or all of the items are mutually exclusive, unless expressly specified otherwise.

It is understood that the use of specific component, device and/or parameter names are for example only and not meant to imply any limitations on the invention. The invention may thus be implemented with different nomenclature/terminology utilized to describe the mechanisms/units/structures/components/devices/parameters herein, without limitation. Each term utilized herein is to be given its broadest interpretation given the context in which that term is utilized.

Terminology. The following paragraphs provide definitions and/or context for terms found in this disclosure (including the appended claims):

"Comprising." This term is open-ended. As used in the appended claims, this term does not foreclose additional structure or steps. Consider a claim that recites: "A memory controller comprising a system cache . . . ." Such a claim does not foreclose the memory controller from including additional components (e.g., a memory channel unit, a switch).

"Configured To." Various units, circuits, or other components may be described or claimed as "configured to" perform a task or tasks. In such contexts, "configured to" or "operable for" is used to connote structure by indicating that the mechanisms/units/circuits/components include structure (e.g., circuitry and/or mechanisms) that performs the task or tasks during operation. As such, the mechanisms/unit/circuit/component can be said to be configured to (or be operable) for perform(ing) the task even when the specified mechanisms/unit/circuit/component is not currently operational (e.g., is not on). The mechanisms/units/circuits/components used with the "configured to" or "operable for" language include hardware—for example, mechanisms, structures, electronics, circuits, memory storing program instructions executable to implement the operation, etc. Reciting that a mechanism/unit/circuit/component is "configured to" or "operable for" perform(ing) one or more tasks is expressly intended not to invoke 35 U.S.C. .sctn.112, sixth paragraph, for that mechanism/unit/circuit/component. "Configured to" may also include adapting a manufacturing process to fabricate devices or components that are adapted to implement or perform one or more tasks.

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

The terms "a", "an" and "the" mean "one or more", unless expressly specified otherwise.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of excludes any element, step, or ingredient not specified in the claim. When the phrase" consists of (or variations thereof) appears in a clause of the body of a claim, rather than immediately following the preamble, it limits only the element set forth in that clause; other elements are not excluded from the claim as a whole. As used herein, the phase "consisting essentially of" and "consisting of" limits the scope of a claim to the specified elements or method steps, plus those that do not materially affect the basis and novel characteristic(s) of the claimed subject matter (see Norian Corp. v Stryker Corp., 363 F.3d 1321, 1331-32, 70 USPQ2d 1508, Fed. Cir. 2004). Moreover, for any claim of the present invention which claims an embodiment "consisting essentially of or" consisting of a certain set of elements of any herein described embodiment it shall be understood as obvious by those skilled in the art that the present invention also covers all possible varying scope variants of any described embodiment(s) that are each exclusively (i.e., "consisting essentially of") functional subsets or functional combination thereof such that each of these plurality of exclusive varying scope variants each consists essentially of any functional subset(s) and/or functional combination(s) of any set of elements of any described embodiment(s) to the exclusion of any others not set forth therein. That is, it is contemplated that it will be obvious to those skilled how to create a multiplicity of alternate embodiments of the present invention that simply consisting essentially of a certain functional combination of elements of any described embodiment(s) to the exclusion of any others not set forth therein, and the invention thus covers all such exclusive embodiments as if they were each described herein.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of", and thus, for the purposes of claim support and construction for "consisting of format claims, such replacements operate to create yet other alternative embodiments" consisting essentially of only the elements recited in the original "comprising" embodiment to the exclusion of all other elements.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

A "computer" may refer to one or more apparatus and/or one or more systems that are capable of accepting a structured input, processing the structured input according to prescribed rules, and producing results of the processing as output. Examples of a computer may include: a computer; a stationary and/or portable computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a client; an interactive television; a web appliance; a telecommunications device with internet access; a hybrid combination of a computer and an interactive television; a portable computer; a tablet personal computer (PC); a personal digital assistant (PDA); a portable telephone; application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, a system on a chip, or a chip set; a data acquisition device; an optical computer; a quantum computer; a biological computer; and generally, an apparatus that may accept data, process data according to one or more stored software programs, generate results, and typically include input, output, storage, arithmetic, logic, and control units.

Those of skill in the art will appreciate that where appropriate, some embodiments of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Where appropriate, embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

"Software" may refer to prescribed rules to operate a computer. Examples of software may include: code segments in one or more computer-readable languages; graphical and or/textual instructions; applets; pre-compiled code; interpreted code; compiled code; and computer programs.

The example embodiments described herein can be implemented in an operating environment comprising computer-executable instructions (e.g., software) installed on a computer, in hardware, or in a combination of software and hardware. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software program code for carrying out operations for aspects of the present invention can be written in any combination of one or more suitable programming languages, including an object oriented programming languages and/or conventional procedural programming languages, and/or programming languages such as, for example, Hyper text Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Wireless Markup Language (WML), Java™, Jini™, C, C++, Smalltalk, Perl, UNIX Shell, Visual Basic or Visual Basic Script, Virtual Reality Markup Language (VRML), ColdFusion™ or other compilers, assemblers, interpreters or other computer languages or platforms.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

A network is a collection of links and nodes (e.g., multiple computers and/or other devices connected together) arranged so that information may be passed from one part of the network to another over multiple links and through various nodes. Examples of networks include the Internet, the public switched telephone network, the global Telex network, computer networks (e.g., an intranet, an extranet, a local-area network, or a wide-area network), wired networks, and wireless networks.

The Internet is a worldwide network of computers and computer networks arranged to allow the easy and robust exchange of information between computer users. Hundreds of millions of people around the world have access to computers connected to the Internet via Internet Service Providers (ISPs). Content providers (e.g., website owners or operators) place multimedia information (e.g., text, graphics, audio, video, animation, and other forms of data) at specific locations on the Internet referred to as webpages. Websites comprise a collection of connected, or otherwise related, webpages. The combination of all the websites and their corresponding webpages on the Internet is generally known as the World Wide Web (WWW) or simply the Web.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The flowchart and block diagrams in the figures illustrate the architecture, functionality, and operation of possible implementations of systems, methods and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

It will be readily apparent that the various methods and algorithms described herein may be implemented by, e.g., appropriately programmed general purpose computers and computing devices. Typically a processor (e.g., a microprocessor) will receive instructions from a memory or like device, and execute those instructions, thereby performing a process defined by those instructions. Further, programs that implement such methods and algorithms may be stored and transmitted using a variety of known media.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The functionality and/or the features of a device may be alternatively embodied by one or more other devices which are not explicitly described as having such functionality/features. Thus, other embodiments of the present invention need not include the device itself.

The term "computer-readable medium" as used herein refers to any medium that participates in providing data (e.g., instructions) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, removable media, flash memory, a "memory stick", any other memory chip or cartridge, a carrier wave as described hereinafter, or any other medium from which a computer can read.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols, such as Bluetooth, TDMA, CDMA, 3G.

Where databases are described, it will be understood by one of ordinary skill in the art that (i) alternative database structures to those described may be readily employed, (ii) other memory structures besides databases may be readily employed. Any schematic illustrations and accompanying descriptions of any sample databases presented herein are exemplary arrangements for stored representations of information. Any number of other arrangements may be employed besides those suggested by the tables shown. Similarly, any illustrated entries of the databases represent exemplary information only; those skilled in the art will understand that the number and content of the entries can be different from those illustrated herein. Further, despite any depiction of the databases as tables, an object-based model could be used to store and manipulate the data types of the present invention and likewise, object methods or behaviors can be used to implement the processes of the present invention.

A "computer system" may refer to a system having one or more computers, where each computer may include a computer-readable medium embodying software to operate the computer or one or more of its components. Examples of a computer system may include: a distributed computer system for processing information via computer systems linked by a network; two or more computer systems connected together via a network for transmitting and/or receiving information between the computer systems; a computer system including two or more processors within a single computer; and one or more apparatuses and/or one or more systems that may accept data, may process data in accordance with one or more stored software programs, may generate results, and typically may include input, output, storage, arithmetic, logic, and control units.

A "network" may refer to a number of computers and associated devices that may be connected by communication facilities. A network may involve permanent connections such as cables or temporary connections such as those made through telephone or other communication links. A network may further include hard-wired connections (e.g., coaxial cable, twisted pair, optical fiber, waveguides, etc.) and/or wireless connections (e.g., radio frequency waveforms, free-space optical waveforms, acoustic waveforms, etc.). Examples of a network may include: an internet, such as the Internet; an intranet; a local area network (LAN); a wide area network (WAN); and a combination of networks, such as an internet and an intranet.

As used herein, the "client-side" application should be broadly construed to refer to an application, a page associated with that application, or some other resource or function invoked by a client-side request to the application. A "browser" as used herein is not intended to refer to any specific browser (e.g., Internet Explorer, Safari, FireFox, or the like), but should be broadly construed to refer to any client-side rendering engine that can access and display Internet-accessible resources. A "rich" client typically refers to a non-HTTP based client-side application, such as an SSH or CFIS client. Further, while typically the client-server interactions occur using HTTP, this is not a limitation either. The client server interaction may be formatted to conform to the Simple Object Access Protocol (SOAP) and travel over HTTP (over the public Internet), FTP, or any other reliable transport mechanism (such as IBM® MQSeries® technologies and CORBA, for transport over an enterprise intranet) may be used. Any application or functionality described herein may be implemented as native code, by providing hooks into another application, by facilitating use of the mechanism as a plug-in, by linking to the mechanism, and the like.

Exemplary networks may operate with any of a number of protocols, such as Internet protocol (IP), asynchronous transfer mode (ATM), and/or synchronous optical network (SONET), user datagram protocol (UDP), IEEE 802.x, etc.

Embodiments of the present invention may include apparatuses for performing the operations disclosed herein. An apparatus may be specially constructed for the desired purposes, or it may comprise a general-purpose device selectively activated or reconfigured by a program stored in the device.

Embodiments of the invention may also be implemented in one or a combination of hardware, firmware, and software. They may be implemented as instructions stored on a machine-readable medium, which may be read and executed by a computing platform to perform the operations described herein.

More specifically, as will be appreciated by one skilled in the art, aspects of the present invention may be embodied as a system, method or computer program product. Accordingly, aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

In the following description and claims, the terms "computer program medium" and "computer readable medium" may be used to generally refer to media such as, but not limited to, removable storage drives, a hard disk installed in hard disk drive, and the like. These computer program products may provide software to a computer system. Embodiments of the invention may be directed to such computer program products.

An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Unless specifically stated otherwise, and as may be apparent from the following description and claims, it should be appreciated that throughout the specification descriptions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Additionally, the phrase "configured to" or "operable for" can include generic structure (e.g., generic circuitry) that is manipulated by software and/or firmware (e.g., an FPGA or a general-purpose processor executing software) to operate in a manner that is capable of performing the task(s) at issue. "Configured to" may also include adapting a manufacturing process (e.g., a semiconductor fabrication facility) to fabricate devices (e.g., integrated circuits) that are adapted to implement or perform one or more tasks.

In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments within the scope of the present disclosure may also include tangible and/or non-transitory computer-readable storage media for carrying or having computer-executable instructions or data structures stored thereon. Such non-transitory computer-readable storage media can be any available media that can be accessed by a general purpose or special purpose computer, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

While a non-transitory computer readable medium includes, but is not limited to, a hard drive, compact disc, flash memory, volatile memory, random access memory, magnetic memory, optical memory, semiconductor based memory, phase change memory, optical memory, periodically refreshed memory, and the like; the non-transitory computer readable medium, however, does not include a pure transitory signal per se; i.e., where the medium itself is transitory.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

FIG. 1 illustrates an exemplary system for testing water, in accordance with an embodiment of the present invention. The system 100 includes at least at least a user 110, a computing system for giving instructions 112, a water testing device 114, a processor 142, and a storage device 118. The computing system 112 may include a display screen 120, a database (not shown in figure), and a data input interface 122.

During a typical operation of the system 100 the user 110 may schedule a test using the computing system 112, the display screen 120, and the data input interface 122. In one embodiment, the test may be scheduled 124 on a dashboard 126. In another embodiment, the test may be scheduled 128 on a mobile application 130. In one embodiment, the dashboard 126 and/or the mobile application 130 may be included in the computing system 112. In another embodiment, the dashboard 126 and/or the mobile application 130 may be included in a mobile device (not shown in figure), wherein the mobile device is in communication with the computing system 112. In yet another embodiment, the computing system 112 may itself represent the mobile device. Accordingly, the computing system 112 or the mobile device includes a designated computer program or algorithm or software capable of sending an order 132 to the water testing device 114 to start a test. The water testing device 114 may include a computing system (not shown in figure) for receiving instructions from computing system 112. The water testing device 114 may start by homing using limit switches. Water from a source 134 may be imported 136 through a feeding peristaltic pump into a testing vial 138 inside the water testing device 114 (shown in call out). It may be appreciated by a person with ordinary skill in the art, in light of and in accordance with the teachings of the present invention, that the source of water may include a tank, a pond or a liquid container that contains the water from a source to be tested. The vial may be flushed and cleaned a few times with the same source of water that is being tested. It may be appreciated by a person of ordinary skill in the art, in light of and in accordance with the teachings of the present invention, that the flushing and cleaning of a vial may be required to ensure that the vial has no other contaminants that may affect the test result of the water being tested. In one embodiment, the vial may be flushed and cleaned for about two times with the water being tested. The water testing device 114 may be programmed using a designated computer program and calibrated to fill the vial with a specific amount of the water sample required for a given test. The water testing device 114 may be programmed using a designated computer program to calibrate the color sensor included in the water testing device 114 with reference to the water sample being tested. The water testing device 114 may be programmed using a designated computer program to position the vial containing the water sample to be tested under a correspondent reagent to be filled in the vial. The water testing device 114 may be programmed using a designated computer program to drop a particular pre calculated amount of the corresponding reagent into the vial containing the water sample being tested. The water testing device 114 may be programmed using a designated computer program to mix the corresponding reagent and the water sample being tested in the vial. It may be appreciated by a person with ordinary skill in the art, in light of and in accordance with the teachings of the present invention, that every reaction requires certain conditions and time for the reaction to take place. Accordingly, the water testing device 114 may be programmed using a designated computer program to provide a specific rest time for each test for the corresponding reagent and the water sample to react. Once the rest/test time is completed a photo colorimeter (not shown in figure) contained in the water testing device 114 may read the color obtained in the vial and generate corresponding results. In an alternative embodiment, instead of dropping a pre-decided amount of reagent in the vial a titration method may be employed to drop a reagent into the water sample being tested. In this embodiment, a drop counter will generate the result. The test results may then be sent 140 to a processor 142. In some embodiments, processor 142 may be included in water testing device 114. In other embodiments, processor 142 may be external to water testing device 114. The results are processed and then sent 144 to a server 118 that includes a designated program/algorithm. In some embodiments, server 118 may be a cloud server. In other embodiments, server 118 may be located on a local network. The dashboard 126 may include a history section for all the water samples and their corresponding measured parameters in figures and in graphs. This information may assist the designated program in improving the test methods and parameters through a process of self-learning. In a non-limiting example, water testing device 114 with processor 142 may learn how much calcium or alkalinity or magnesium may be used from the tested water, such as but not limited to, aquarium water, and may later give orders to another device to dose the missing element. In one embodiment, the water may be tested for dissolved substances.

It may be appreciated by a person with ordinary skill in the art, in light of and in accordance with the teachings of the present invention, the computing system 112 may connect to any number of devices with virtually any wired and/or wireless means. The computing system 112 may connect to virtually any device by means such as, but not limited to, Bluetooth connection, Ethernet cable, USB cable, WIFI, IRDA, etc. In an alternative embodiment of the present invention, the computing system 112 may send the test schedule to the water testing device via a cellular connection.

In some embodiments, computing system 112 may comprise a smartphone. It may be appreciated by a person with ordinary skill in the art, in light of and in accordance with the teachings of the present invention, smartphone 112 may be any device capable of capturing an image. Smartphone 112 may be devices such as, but not limited to, digital cameras, web cameras, video cameras, etc. In another embodiment of the present invention, smartphone 112 may be an integrated web camera on a personal computer, tablet or laptop.

It may be appreciated by a person with ordinary skill in the art, in light of and in accordance with the teachings of the present invention, server 118 may be virtually any computing platform such as, but not limited to, a computer cluster, a laptop, a tablet, a smartphone, etc. In another embodiment of the present invention, server 118 may be a cloud based server or IOT based server. The server 118 may be capable of sharing the results of the water testing with others who have a need for the data with the authorization of the user. The server 118 may also be capable of sending alerts to the user for scheduling the water tests or alerts on any parameters going askew and provide data to populate the dashboard used by the user to schedule the tests. The historical data stored in the dashboard may also be stored in the server 118 and accessed from the server 118 by authorized persons.

It may be appreciated by a person with ordinary skill in the art, in light of and in accordance with the teachings of the present invention, a dashboard 126 may be virtually any platform that enables a user to manage tests, test results, historical data, test scheduling, maintain alerts, design tests, and the like. Dashboard may be, but not limited to, an excel spread sheet, or database.

It may be appreciated by a person with ordinary skill in the art, in light of and in accordance with the teachings of the present invention, a database (not shown in figure) may be virtually any data storage device or devices. Database may be, but not limited to, a plurality of data servers, a memory card. In another embodiment of the present invention, database may be a memory card connected to server 118.

It may be appreciated by a person with ordinary skill in the art, in light of and in accordance with the teachings of the present invention, that database may contain virtually any data to improve the functionality of water testing system 100. Database may include, without limitation, typical problems associated with water sources, resolution libraries, corresponding reagent lists, lists of potential dissolved matter in water, historical data on the water samples from a particular source, and the like. In another embodiment of the present invention, database may contain a table storing one or more dashboards/algorithms that enable the user to schedule a test without having to repeatedly enter the data for scheduling a test.

It may be appreciated by a person with ordinary skill in the art, in light of and in accordance with the teachings of the present invention, the designated computer program for the system of water testing 100 may partially or completely contained in a local computing platform and/or network that includes the water testing device 114.

Figure 2:
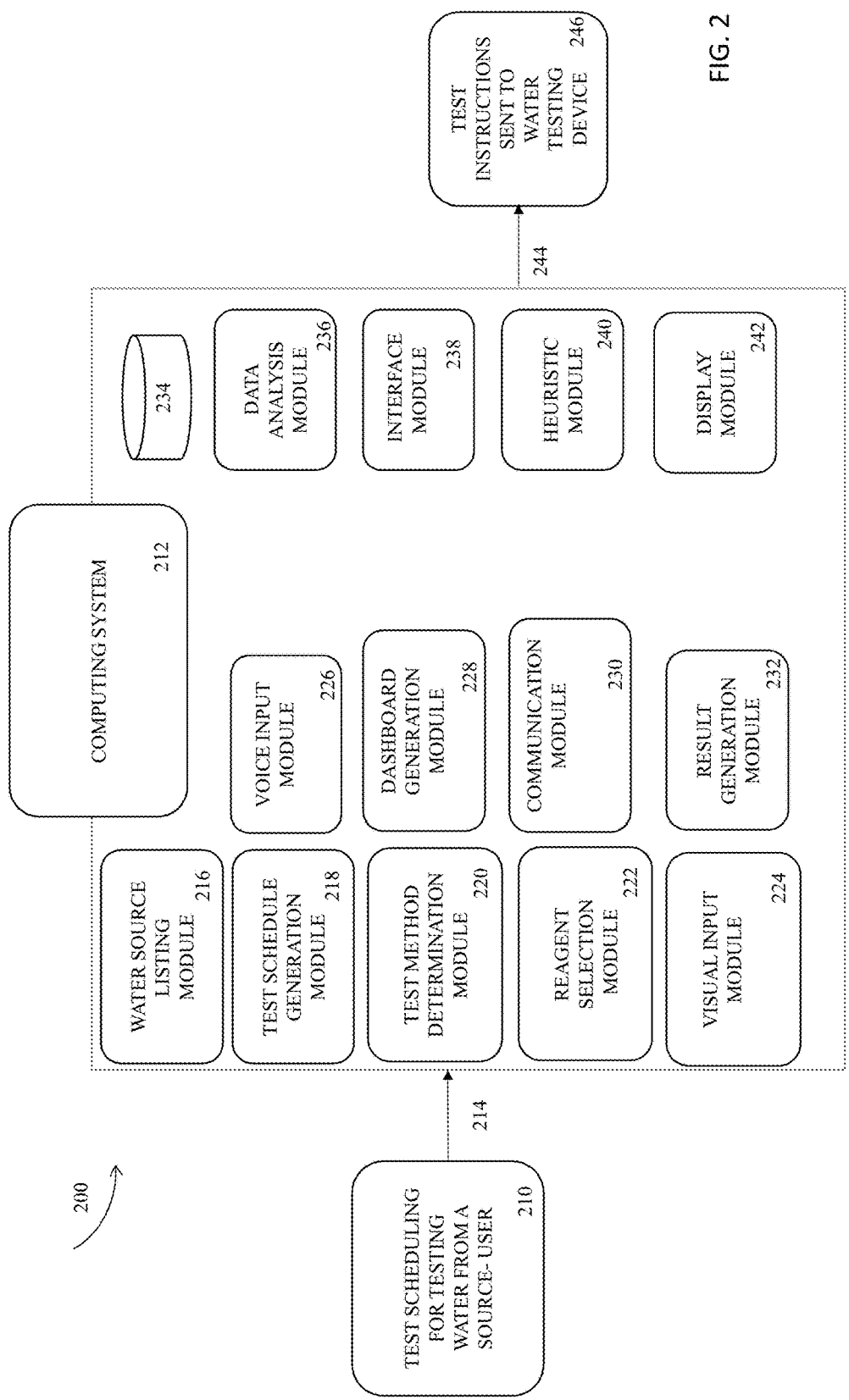
FIG. 2 illustrates an architecture of an exemplary system for testing water, in accordance with an embodiment of the present invention.

FIG. 2 illustrates an architecture of an exemplary system 200 for testing water, in accordance with an embodiment of the present invention. The system 200 provides the architecture for computing system for (giving instructions) 212 to a water testing machine. The computing system 112 architecture in a system for testing water may include a water source listing module 216, a test schedule generation module 218, a test method determination module 220, a reagent selection module 222, a visual input module 224, a voice input module 226, a dashboard generation module 228, a communication module 230, a result generation module 232, a database 234, a data analysis module 234, a interface module 238, a heuristic module 240, and a display module 242. The water source listing module 216 may have a means of listing and prioritizing the sources of water to be tested in a given area, such as, without limitation, sensors and/or a processing unit, and providing a list of water sources on a display 120. A test schedule generation module 218 may have a means of prioritizing and scheduling the sources of water to be tested in a given area, such as, without limitation, sensors and/or a processing unit, and providing a test schedule for the water sources on a display 120. A test determination module 220 may have a means of determining the tests required to be performed on the sources of water to be tested in a given area, such as, without limitation, sensors and/or a processing unit, and providing a pre-determined test for the water sources on a display 120. A reagent selection module 222 may have a means of selecting the reagents that may be required based on the pre-determined tests required to be performed on the sources of water to be tested in a given area, such as, without limitation, sensors and/or a processing unit, and providing a reagent list required for testing the water sources on a display 120. The visual input module 224 may have a means of processing an image such as, without limitation, a processing unit, a computer, or a server to execute computer code and/or algorithms from a non-transitory computer readable medium for image recognition. A visual input module 224 may have a means of providing a visual input to the computing system 212 for selecting new water sources or prioritizing the water source list for scheduling a test based on visual evaluation of the water, such as, without limitation, optic sensors and/or a processing unit, and providing a visual input for listing and scheduling a water source for testing. The voice input module 226 may have a means of processing a voice such as, without limitation, a processing unit, a computer, or a server to execute computer code and/or algorithms from a non-transitory computer readable medium for voice recognition. A voice input module 226 may have a means of enabling the user to provide vocal instructions to the computing system 212 for selecting, scheduling, and determining tests, such as, without limitation, voice receptors and/or a processing unit, and providing a sound input for listing and scheduling a water source for testing. The voice input module 226 and the visual input module 224 may also be used for security purposes to ensure that the user is authorized to use the water testing system 100. The dashboard generation module 228 may have a means of generating a dashboard such as, without limitation, a processing unit, a computer, or a server to execute computer code and/or algorithms from a non-transitory computer readable medium for generating a dashboard for the water sources, tests scheduled, tests to be performed for each water resources etc. . . . and providing the dashboard on a display 120. A communication module 230, may have a means of communicating such as, without limitation, a processing unit, a computer, or a server to execute computer code and/or algorithms from a non-transitory computer readable medium for communicating the information from the dashboard to the water testing device 114. A result generation module 232 may have a means of generating results, such as, without limitation, a processing unit, a computer, or a server to execute computer code and/or algorithms from a non-transitory computer readable medium for populating the dashboard 126. A database 234 may have a means for storing data, such as, without limitation, a processing unit, a computer, or a server to execute computer code and/or algorithms from a non-transitory computer readable medium for providing current data, historical data, statutory data, etc. . . . for populating the dashboard 126. A data analysis module 234 may have a processing means such as, without limitation, a processing unit, a computer, or a server to execute computer code and/or algorithms from a non-transitory computer readable medium for analyzing the various data inputs and providing the analysis to the user to determine data for populating the dashboard 126. An interface module 238 may have a processing means such as, without limitation, a processing unit, a computer, or a server to execute computer code and/or algorithms from a non-transitory computer readable medium for transmitting/communicating test schedules via the communication module to the water testing machine 114. A heuristic module 240 may have a processing means such as, without limitation, a processing unit, a computer, or a server to execute computer code and/or algorithms from a non-transitory computer readable medium for processing the data/information provided by the data analyzing module and providing pointers to the user based on a self-learning model. It may be appreciated by a person with ordinary skill in the art, in light of and in accordance with the teachings of the present invention, that virtually any algorithm and/or computer code may be used to self-learn using the heuristic module 240. In a non-limiting example, self-learning algorithms and/or methods may include, without limitation, machine learning the curve of alkalinity, calcium, magnesium usage of a reef aquarium. A display module 242 may have a means to display the dashboard and other lists used to generate the dashboard, such as, without limitation, a screen 120 on a computing system 212, to a user.

It may be appreciated by a person with ordinary skill in the art, in light of and in accordance with the teachings of the present invention, that one or more modules may be embodied in a single device. In an alternative embodiment of the present invention, all modules may be embodied in a desktop, except the data analysis module and the dashboard generation module, that may be embodied in a smartphone device, which would be capable of enabling a user to generate the dashboard and send communication to the water testing device 114.

During an operation of the computing system for giving instructions 212 to a water testing machine 114 the user 210 uses 214 the computing system 212 to generate 244 test instructions that are sent 246 to the water testing device 246

It may be appreciated by a person with ordinary skill in the art, in light of and in accordance with the teachings of the present invention, that virtually any algorithm and/or computer code may be used to recognize an image on visual input module 224. Image recognition algorithms and/or methods may include, without limitation, Bayesian networks, fuzzy logic, neural networks, template matching, Hidden Markov models, machine learning, data mining, feature extraction and data analysis/statistics, optical character recognition, etc. In an alternative embodiment of the present invention, a binary search tree may be implemented to extra data from an image.

It may be appreciated by a person with ordinary skill in the art, in light of and in accordance with the teachings of the present invention, that there may be a plurality of the same modules in the computing system for giving instructions 212 to a water testing machine 114. A plurality of modules such as, without limitation, a water source listing module 216, a test schedule generation module 218, a test method determination module 220, a reagent selection module 222, a visual input module 224, a voice input module 226, a dashboard generation module 228, a communication module 230, a result generation module 232, a database 234, a data analysis module 234, a interface module 238, a heuristic module 240, and a display module 242 may be present in the computing system (for giving instructions) 212 to a water testing machine 114. The plurality of similar modules may work in parallel or independently to improve the throughput and/or speed the computing system (for giving instructions) 212 to a water testing machine 114. In an alternative embodiment of the present invention, a plurality of recognition and/or solution modules may be connected to the computing system (for giving instructions) 212 to a water testing machine 114 via wired and wireless connections to access resources from different wired and wireless networks. In still another alternative embodiment of the present invention, a plurality of similar modules may form a secondary computing system for giving instructions 212 to a water testing machine 114 capable of seamlessly substituting a messing and/or failing module.

It may be appreciated by a person with ordinary skill in the art, in light of and in accordance with the teachings of the present invention, that one or more modules may transmit water testing information to a tech support server that is on an accessible network or over the internet. In an alternative embodiment of the present invention, additional water testing information may be sent to a server to alleviate processing load on a water testing device 114.

It may be appreciated by a person with ordinary skill in the art, in light of and in accordance with the teachings of the present invention, that any module in computing system (for giving instructions) 212 to a water testing machine 114 may perform data manipulation. Data manipulation such as, but not limited to, compression, encryption, formatting, and the like. In an alternative embodiment of the present invention, any module sending data may first compress the data prior to data transmission.

Figure 3:
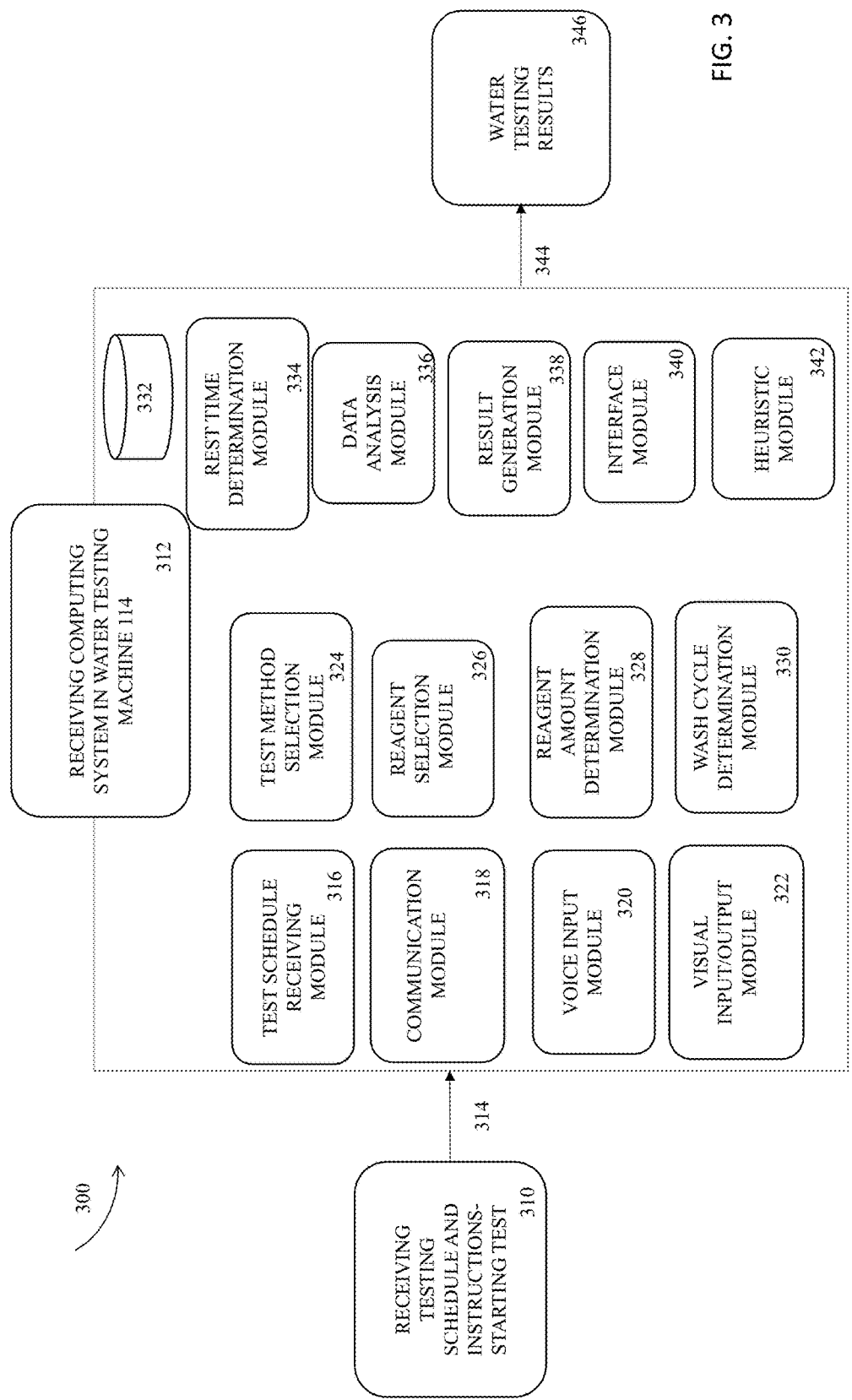
FIG. 3 illustrates an architecture of an exemplary system for testing water, in accordance with an embodiment of the present invention.

FIG. 3 illustrates an architecture of an exemplary system 300 for testing water, in accordance with an embodiment of the present invention. The system 300 provides the architecture for a computing system for (receiving instructions) 312 in a water testing machine 114. The computing system 312 architecture in a system for testing water may include a test schedule receiving module 316, a communication module 318, a voice input module 320, a visual input/output module 322, a test method selection module 324, a reagent selection module 326, a reagent amount determination module 328, a wash cycle determination module 330, a rest time determination module 334, a data analysis module 336, a result generation module 338, an interface module 340, and a heuristic module 342. A test schedule receiving module 316 may have a means of processing information such as, without limitation, a processing unit, a computer, or a server to execute computer code and/or algorithms from a non-transitory computer readable medium for test schedule processing and accordingly scheduling and prioritizing the sources of water to be tested in a given area. A communication module 318, may have a means of communicating such as, without limitation, a processing unit, a computer, or a server to execute computer code and/or algorithms from a non-transitory computer readable medium for communicating the information from the water testing device 114 to the processor 142. A visual input module 320 may have a means of processing an image such as, without limitation, a processing unit, a computer, or a server to execute computer code and/or algorithms from a non-transitory computer readable medium for color recognition. A visual input module 320 may have a means of providing a visual input to the computing system 312 for determining a visual test result performed by the water testing device 114, for example, using a photocolorimeter. The voice input/output module 322 may have a means of processing a voice such as, without limitation, a processing unit, a computer, or a server to execute computer code and/or algorithms from a non-transitory computer readable medium for voice recognition/ emission. A voice input module 322 may have a means of enabling the computing system 212 to provide voice alerts to computing system 312 for performing the various steps like selecting, scheduling, and determining tests, such as, without limitation, voice receptors and/or a processing unit, and providing a sound input/output for listing and scheduling a water source for testing. In certain embodiments, the voice input module 320 and the visual input/output module 322 may also be used for security purposes to ensure that the user is authorized to use the water testing system 100. A test method selection module 324 may have a means of processing information such as, without limitation, a processing unit, a computer, or a server to execute computer code and/or algorithms from a non-transitory computer readable medium for selecting an appropriate test and accordingly scheduling and prioritizing the type of tests to be conducted for a given source of water. A reagent selection module 326 may have a means of processing information such as, without limitation, a processing unit, a computer, or a server to execute computer code and/or algorithms from a non-transitory computer readable medium for selecting an appropriate reagent for a given test to be conducted for a given source of water. A reagent amount determination module 328 may have a means of processing information such as, without limitation, a processing unit, a computer, or a server to execute computer code and/or algorithms from a non-transitory computer readable medium for selecting an appropriate amount of reagent for a given test to be conducted for a given source of water. A wash cycle determination module 330 may have a means of processing information such as, without limitation, a processing unit, a computer, or a server to execute computer code and/or algorithms from a non-transitory computer readable medium for selecting an appropriate number of times to wash a vial with a given source of water to be tested before conducting the test for the given source of water. A database 332 may have a means for storing data, such as, without limitation, a processing unit, a computer, or a server to execute computer code and/or algorithms from a non-transitory computer readable medium for providing current data, historical data, statutory data, etc. . . . for data analysis. A rest time determination module 334 may have a means of processing information such as, without limitation, a processing unit, a computer, or a server to execute computer code and/or algorithms from a non-transitory computer readable medium for selecting an appropriate time of rest after a reagent is added to the given source of water in the vial. A data analysis module 336 may have a processing means such as, without limitation, a processing unit, a computer, or a server to execute computer code and/or algorithms from a non-transitory computer readable medium for analyzing the various data inputs and providing the analysis to the user to determine the quality of the tested water. A result generation module 338 may have a means of generating results, such as, without limitation, a processing unit, a computer, or a server to execute computer code and/or algorithms from a non-transitory computer readable medium for providing the test results for the water. An interface module 340 may have a processing means such as, without limitation, a processing unit, a computer, or a server to execute computer code and/or algorithms from a non-transitory computer readable medium for transmitting/communicating test results via the communication module 318 to the processor 142. A heuristic module 342 may have a processing means such as, without limitation, a processing unit, a computer, or a server to execute computer code and/or algorithms from a non-transitory computer readable medium for processing the data/information provided by the data analysis module and providing pointers to the user based on a self-learning model. As discussed hereinabove, it may be appreciated by a person with ordinary skill in the art, in light of and in accordance with the teachings of the present invention, that virtually any algorithm and/or computer code may be used to self-learn using the heuristic module 342.

It may be appreciated by a person with ordinary skill in the art, in light of and in accordance with the teachings of the present invention, that one or more modules may be embodied in a single device. In an alternative embodiment of the present invention, all modules may be embodied in the water testing device 114, except for the data analysis module and the result generation module that may be embodied in a smartphone device which would be capable of enabling a user to generate the results and send communication to the processor 142.

During an operation of the computing system for receiving instructions 312 in a water testing machine 114 the testing schedule and instructions for starting the test 310 are received 314 by the computing system 312 to generate 344 test results 346.

It may be appreciated by a person with ordinary skill in the art, in light of and in accordance with the teachings of the present invention, that virtually any algorithm and/or computer code may be used to recognize an image on visual input module 320. Image recognition algorithms and/or methods may include, without limitation, Bayesian networks, fuzzy logic, neural networks, template matching, Hidden Markov models, machine learning, data mining, feature extraction and data analysis/statistics, optical character recognition, etc. In an alternative embodiment of the present invention, a binary search tree may be implemented to extra data from an image.

It may be appreciated by a person with ordinary skill in the art, in light of and in accordance with the teachings of the present invention, that there may be a plurality of the same modules in the computing system for receiving instructions 312 in a water testing machine 114. A plurality of modules such as, without limitation, a test schedule receiving module 316, a communication module 318, a voice input module 320, a visual input/output module 322, a test method selection module 324, a reagent selection module 326, a reagent amount determination module 328, a wash cycle determination module 330, a rest time determination module 334, a data analysis module 336, a result generation module 338, an interface module 340, and a heuristic module 342 may be present in the computing system (for receiving instructions) 312 in a water testing machine 114. The plurality of similar modules may work in parallel or independently to improve the throughput and/or speed the computing system (for receiving instructions) 312 in a water testing machine 114. In an alternative embodiment of the present invention, a plurality of recognition and/or solution modules may be connected to the computing system (for receiving instructions) 312 in a water testing machine 114 via wired and wireless connections to access resources from different wired and wireless networks. In still another alternative embodiment of the present invention, a plurality of similar modules may form a secondary computing system (for receiving instructions) 312 in a water testing machine 114 capable of seamlessly substituting a missing and/or failing module.

It may be appreciated by a person with ordinary skill in the art, in light of and in accordance with the teachings of the present invention, that one or more modules may transmit water testing information to a tech support server that is on an accessible network or over the internet. In an alternative embodiment of the present invention, additional water testing information may be sent to a server to alleviate processing load on a water testing device 114.

It may be appreciated by a person with ordinary skill in the art, in light of and in accordance with the teachings of the present invention, that any module in computing system (for receiving instructions) 312 in a water testing machine 114 may perform data manipulation. Data manipulation such as, but not limited to, compression, encryption, formatting, and the like. In an alternative embodiment of the present invention, any module receiving data may first decompress the data prior to data assimilation.

Figure 4:
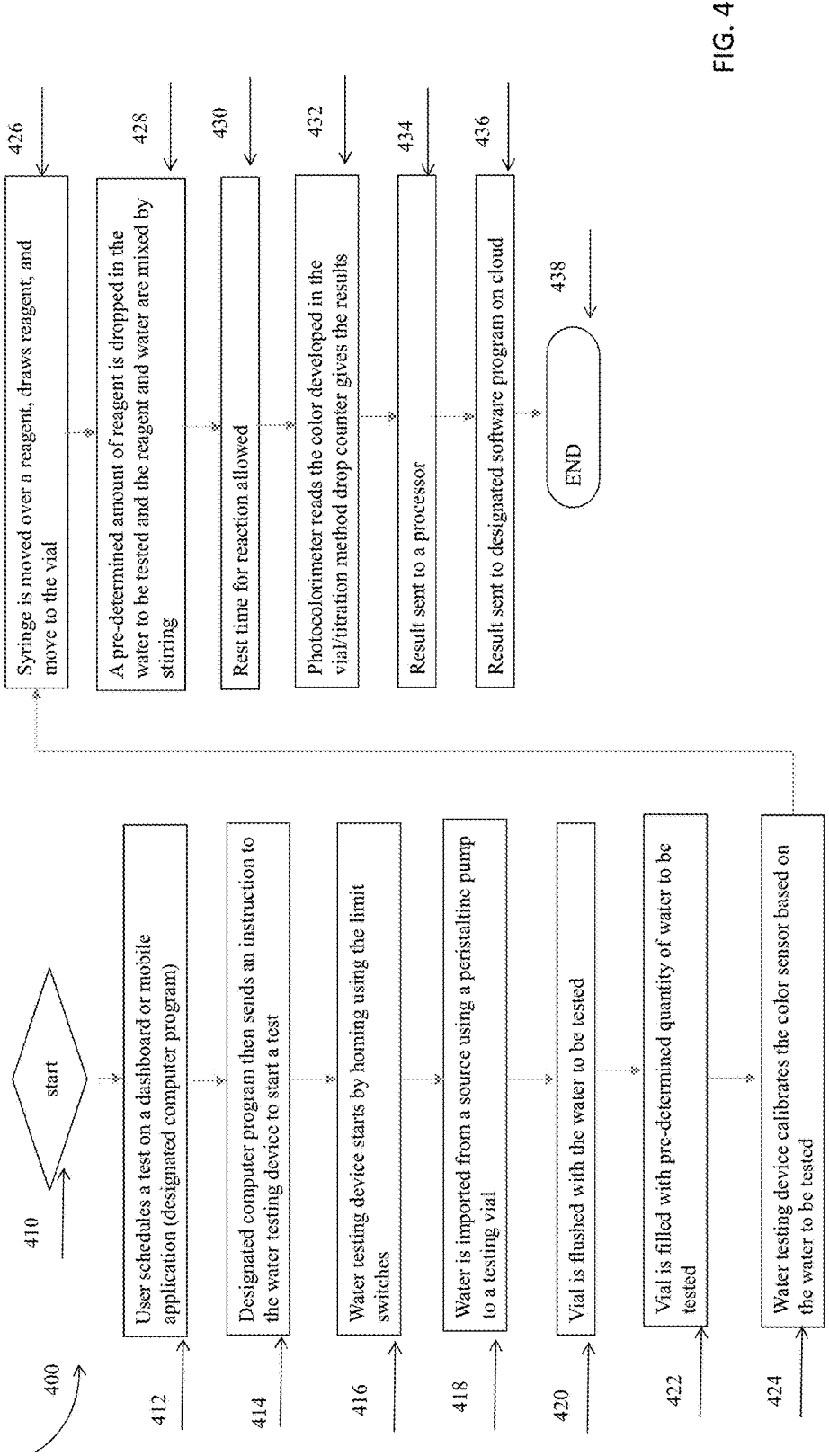
FIG. 4 is a flow chart illustrating an exemplary process for testing water, in accordance with an embodiment of the present invention.

FIG. 4 provides a flow chart 400 illustrating an exemplary process for testing water, in accordance with an embodiment of the present invention. The process shown in flow chart 400 starts with a step 410. In step 412 a user 110 may schedule a test using the computing system 112, the display screen 120, and the data input interface 122. In one embodiment, the test may be scheduled 124 on a dashboard 126. In another embodiment, the test may be scheduled 128 using a mobile application 130. In a step 414 a designated computer program or algorithm or software capable of sending an order 132 included in the computing system 112 or the mobile device sends an order to the water testing device 114 to start a test. In a step 416 the water testing device 114 may start by homing using limit switches. In a step 418 water from a source 134 may be imported 136 through a feeding peristaltic pump into a testing vial 138 inside the water testing device 114 (shown in call out). In a step 420 the vial may be flushed and cleaned a few times with the same source of water that is being tested. In a step 422 the vial is filled with a pre-determined quantity of water to be tested. In a step 424 the water testing device calibrates a color sensor based on the water to be tested. In exemplary embodiments, the color sensor may include, but may not be limited to, USB Camera, TCS3200, TCS3414, and silicon photodiodes. In a step 426 a syringe may be moved above a reagent vial, draws the reagent from the reagent vial and then may be moved by the water testing machine to position the syringe over the vial. In some embodiments, prior to drawing the reagent, the syringe may be rinsed and cleaned with a purified water such as, but not limited to, water that has been passed through a Reverse Osmosis and De-Ionization (RODI) system. In a step 428 a pre-determined amount of reagent is dropped into the vial containing the water sample being tested and the reagent and the water are stirred together in the vial. In some embodiments, after dropping the reagent, the syringe may be rinsed and cleaned with RODI water. In some embodiments, the reagent and water to be tested may be stirred in the vial by a stirrer such as, but not limited to, a magnetic stirrer. In some embodiments, a calculation is made of the amount of reagent dropped from the syringe. In a step 430 a specific rest time is provided for each test for the reagent and the water sample to react. In a step 432, in one embodiment a photocolorimeter contained in the water testing device 114 may read the color obtained in the vial and generate corresponding results. In a step 432 in an alternative embodiment, instead of dropping a pre-decided amount of reagent in the vial a titration method may be employed to drop a reagent into the water sample being tested. In this embodiment, a drop counter may generate the result. In a step 434 the test results may be sent to a processor 142. In a step 436, the results may be sent to a cloud server 118 that includes a designated program/algorithm. In some embodiments the results may be sent to dashboard 126. The process ends with a step 438.

It may be appreciated by a person with ordinary skill in the art, in light of and in accordance with the teachings of the present invention, that virtually any additional steps may be added to the water testing process 400. Additional steps may include, but not limited to, additional data gathering, sending messages to other devices, and accessing additional resources. In yet another alternative embodiment of the present invention, the water testing process 400 may include suggesting recommended resolutions to a user before and/or after the designated computer program captures user information.

It may be appreciated by a person with ordinary skill in the art, in light of and in accordance with the teachings of the present invention, that one or more steps in the water testing process 400 may be added, removed, or rearranged. In other embodiments of the present invention, the order of steps in the water testing process 400 may occur in any order. In still other embodiments of the present invention, additional steps may be added to the water testing process 400.

It may be appreciated by a person with ordinary skill in the art, in light of and in accordance with the teachings of the present invention, that various sources of water may have various dissolved and suspended elements present. Accordingly, for every given source of water to be tested may require a different test protocol and test schedule based on the source of the water. In certain embodiments, statutory requirements may also dictate the test protocols and testing schedules for a source of water. The sources of water may include, but are not limited to well, river, pond, aquarium, storage tanks, water in water containers, and the like.

In various embodiments, the different parameters that may be tested include but are not limited to pH, i.e., acidity and alkalinity of water; dissolved salts, i.e., calcium salts, phosphates, nitrates, magnesium, copper salts, and the like; dissolved oxygen etc. . . . . .

In various embodiments, the system may require minimum human intervention i.e., for using the dashboard or mobile application to order the tests, to refill the reagents in the water testing device, etc. . . . . . Automating the water testing process provides improved accuracy in the results. In one embodiment, the user can view the history in the dashboard; receiver alerts on test scheduling, reagent filling etc . . . ; and schedule a test from a remote location. The water testing machine in this embodiment may be located closer to the source of water to be tested. In certain embodiments, the user and the water testing device may be located in close proximity to the source of water to be tested. In one embodiment, since the results are translated from color value to number value, even color blind users are enabled to use the system for water testing disclosed herein.

It may be appreciated by a person with ordinary skill in the art, in light of and in accordance with the teachings of the present invention, that various reagents may be employed based on the test determined for a given source of water. For example, the reagents employed for chlorine may include, but are not limited to, DPD (N,N Diethyl-1,4 Phenylenediamine Sulfate). For example, the reagents employed for magnesium may include, but are not limited to, Ammoniacal buffer (pH 10) Range from 30 ppm to 1500 ppm. For example, the reagents employed for alkalinity may include, but are not limited to, 0.048% W/W of Bromocresol green and Methyl red 5:1 ratio Range 0.00 dKh to 15.7 dKh. For example, the reagents employed for calcium may include, but are not limited to, one molar NaOH solution, which include anhydrous sodium hydroxide pellets in 30 ml deionized water. Range 10 ppm to 500 ppm. The amount of reagent required to perform the tests are in drops. A maximum of 50 drops per test and a minimum of 1 drop. The tests are based on the Standard Methods for the Examination of Water and Wastewater Standard Methods is a joint publication of the American Public Health Association (APHA), the American Water Works Association (AWWA), and the Water Environment Federation (WEF). (https://www.standard-methods.org/)

Figure 5:
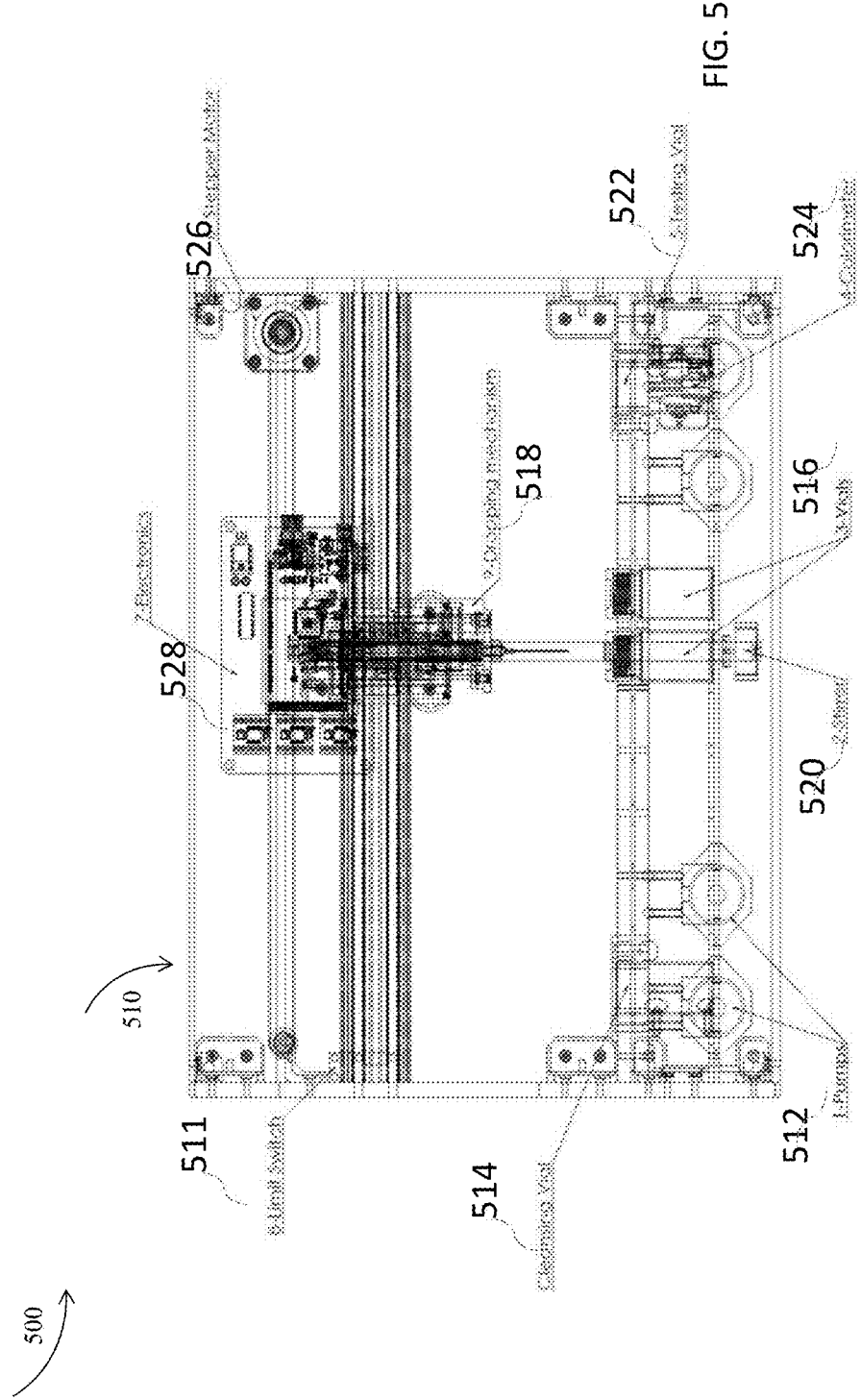
FIG. 5 illustrates a frontal view of an exemplary device for testing water, in accordance with an embodiment of the present invention.

FIG. 5 illustrates a frontal view 500 of an exemplary device for testing water, in accordance with an embodiment of the present invention. The frontal view 500 shows the limit switches 511 used by the water testing device 510 to start the device. The front view also shows the peristaltic pumps that are employed to pump water to be tested from a source into the vials in a water testing device 510. The position indicated by arrow 514 shows the location of the vials when the vials are cleaned with the water to be tested before filling the vials with a test sample of the water to be tested. The vials 516 (two vials shown in view 500) are positioned under the dropping mechanism. The reagents (not shown in figure) are dropped into the vials as described hereinabove. The vials are then stirred using stirrer 520 to ensure mixing of the water with the reagents. The vials are then allowed to rest for the reaction to complete. The vials are then moved in position 522 and the colorimeter 524 reads the color developed in the vials and provides the results. The vials, stirrer, and the dropping mechanism may be moved using the motor 526. The computing system 312 may be included in the portion 528 above the dropping mechanism.

Figure 6:
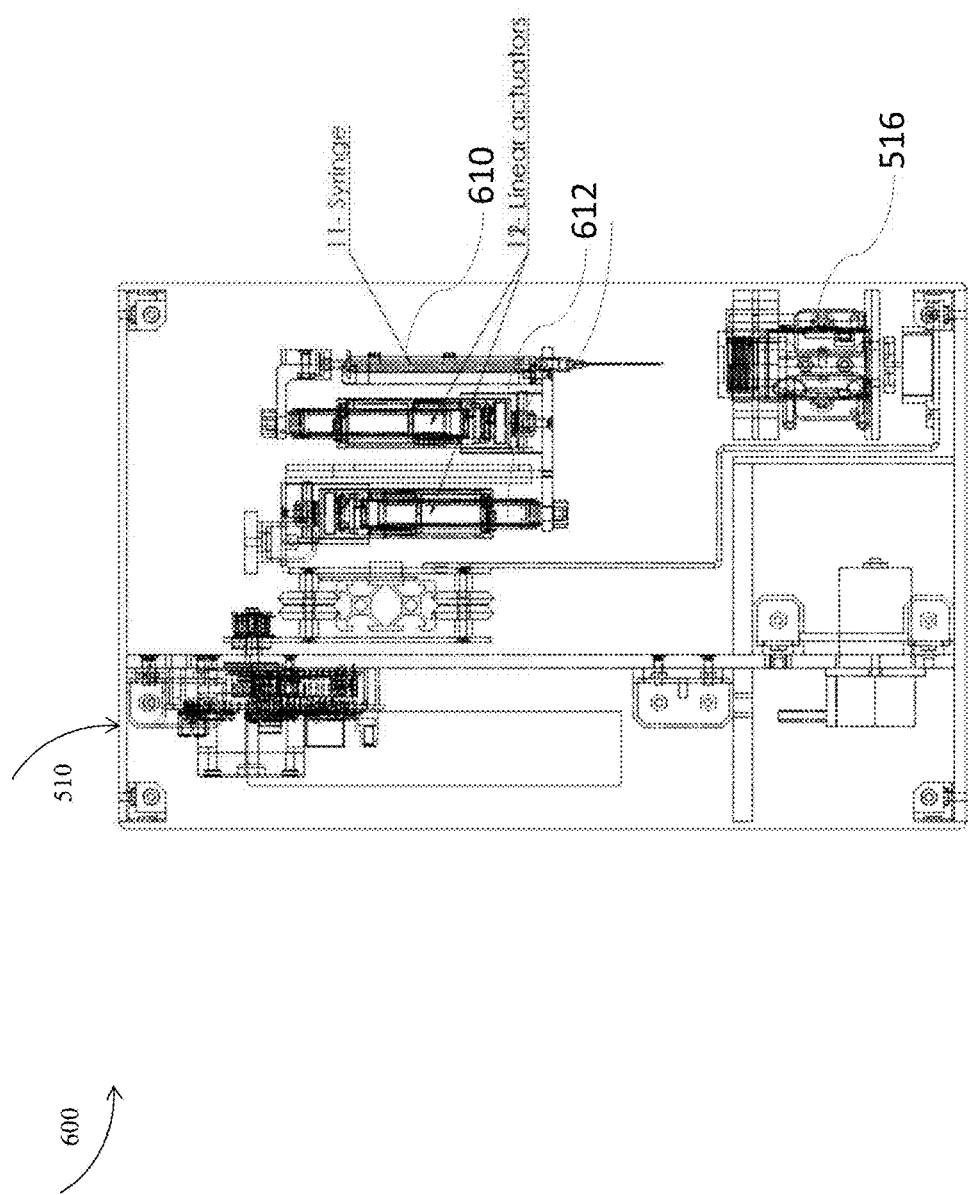
FIG. 6 illustrates a side view of an exemplary device for testing water, in accordance with an embodiment of the present invention.

FIG. 6 illustrates a side view of an exemplary device for testing water, in accordance with an embodiment of the present invention. The side view 600 shows the syringe 612 that may be used to drop the reagent into the vial 516. The side view 600 of the water testing device 510 also shows the linear actuators 610 used for controlling the syringe and the pusher of the syringe. Testing device 510 may have, but not limited to, dimensions of width 42.5 cm, depth 22 cm, and height 33.5 cm. It may be appreciated by a person with ordinary skill in the art, in light of and in accordance with the teachings of the present invention, that device 510 may be constructed having smaller or larger dimensions.

Figure 7A:
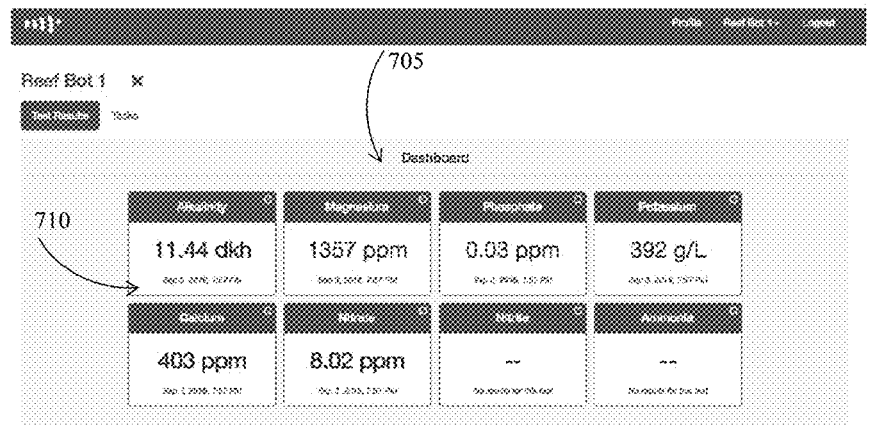
FIGS. 7a and 7b illustrate exemplary test results, in accordance with an embodiment of the present invention.
Figure 7B:
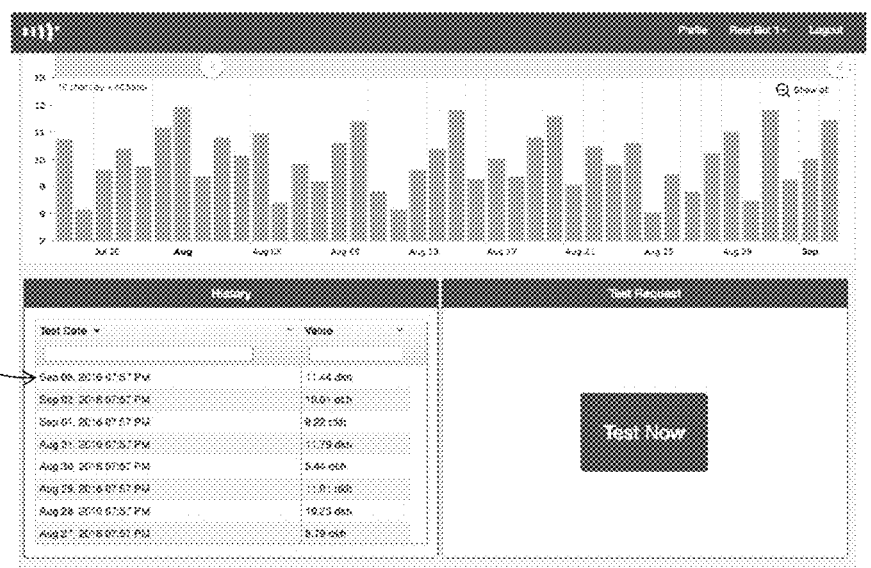

FIGS. 7a and 7b illustrate exemplary test results, in accordance with an embodiment of the present invention. FIG. 7a illustrates a plurality of test results 705 on a water source for a given day. FIG. 7b illustrates a history of a selected test 710 over a period of time. These results may be displayed, for example, but not limited to, on dashboard 126.

Those skilled in the art will readily recognize, in light of and in accordance with the teachings of the present invention, that any of the foregoing steps and/or system modules may be suitably replaced, reordered, removed and additional steps and/or system modules may be inserted depending upon the needs of the particular application, and that the systems of the foregoing embodiments may be implemented using any of a wide variety of suitable processes and system modules, and is not limited to any particular computer hardware, software, middleware, firmware, microcode and the like. For any method steps described in the present application that can be carried out on a computing machine, a typical computer system can, when appropriately configured or designed, serve as a computer system in which those aspects of the invention may be embodied.

Figure 8:
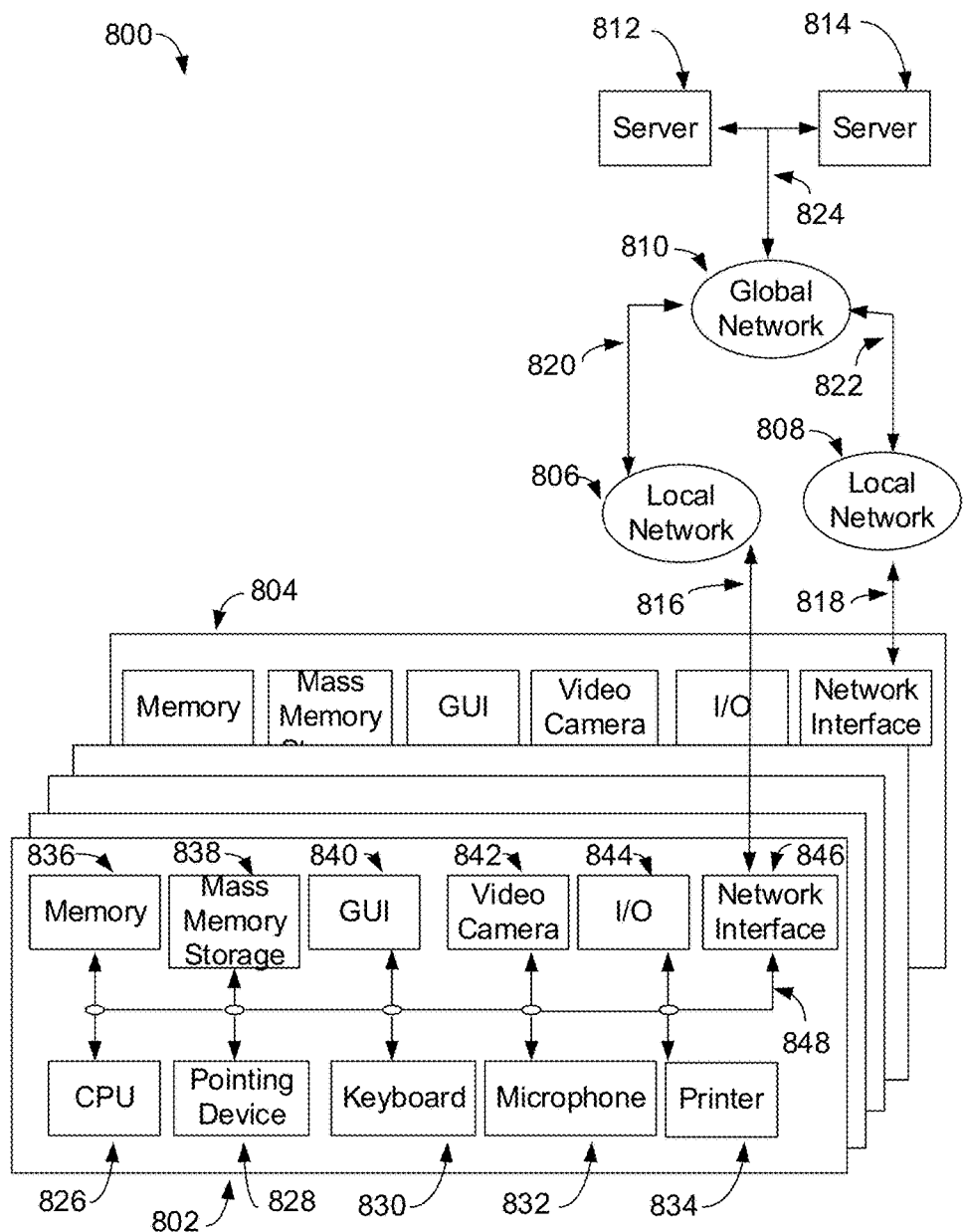
FIG. 8 is a block diagram depicting an exemplary client/server system which may be used by an exemplary web-enabled/networked embodiment of the present invention.

FIG. 8 is a block diagram depicting an exemplary client/server system which may be used by an exemplary web-enabled/networked embodiment of the present invention.

A communication system 800 includes a multiplicity of clients with a sampling of clients denoted as a client 802 and a client 804, a multiplicity of local networks with a sampling of networks denoted as a local network 806 and a local network 808, a global network 810 and a multiplicity of servers with a sampling of servers denoted as a server 812 and a server 814.

Client 802 may communicate bi-directionally with local network 806 via a communication channel 816. Client 804 may communicate bi-directionally with local network 808 via a communication channel 818. Local network 806 may communicate bi-directionally with global network 810 via a communication channel 820. Local network 808 may communicate bi-directionally with global network 810 via a communication channel 822. Global network 810 may communicate bi-directionally with server 812 and server 814 via a communication channel 824. Server 812 and server 814 may communicate bi-directionally with each other via communication channel 824. Furthermore, clients 802, 804, local networks 806, 808, global network 810 and servers 812, 814 may each communicate bi-directionally with each other.

In one embodiment, global network 810 may operate as the Internet. It will be understood by those skilled in the art that communication system 800 may take many different forms. Non-limiting examples of forms for communication system 800 include local area networks (LANs), wide area networks (WANs), wired telephone networks, wireless networks, or any other network supporting data communication between respective entities.

Clients 802 and 804 may take many different forms. Non-limiting examples of clients 802 and 804 include personal computers, personal digital assistants (PDAs), cellular phones and smartphones.

Client 802 includes a CPU 826, a pointing device 828, a keyboard 830, a microphone 832, a printer 834, a memory 836, a mass memory storage 838, a GUI 840, a video camera 842, an input/output interface 844, and a network interface 846.

CPU 826, pointing device 828, keyboard 830, microphone 832, printer 834, memory 836, mass memory storage 838, GUI 840, video camera 842, input/output interface 844 and network interface 846 may communicate in a unidirectional manner or a bi-directional manner with each other via a communication channel 848. Communication channel 848 may be configured as a single communication channel or a multiplicity of communication channels.

CPU 826 may be comprised of a single processor or multiple processors. CPU 826 may be of various types including micro-controllers (e.g., with embedded RAM/ROM) and microprocessors such as programmable devices (e.g., RISC or SISC based, or CPLDs and FPGAs) and devices not capable of being programmed such as gate array ASICs (Application Specific Integrated Circuits) or general purpose microprocessors.

As is well known in the art, memory 836 is used typically to transfer data and instructions to CPU 826 in a bi-directional manner. Memory 836, as discussed previously, may include any suitable computer-readable media, intended for data storage, such as those described above excluding any wired or wireless transmissions unless specifically noted. Mass memory storage 838 may also be coupled bi-directionally to CPU 826 and provides additional data storage capacity and may include any of the computer-readable media described above. Mass memory storage 838 may be used to store programs, data and the like and is typically a secondary storage medium such as a hard disk. It will be appreciated that the information retained within mass memory storage 838, may, in appropriate cases, be incorporated in standard fashion as part of memory 836 as virtual memory.

CPU 826 may be coupled to GUI 840. GUI 840 enables a user to view the operation of computer operating system and software. CPU 826 may be coupled to pointing device 828. Non-limiting examples of pointing device 828 include computer mouse, trackball and touchpad. Pointing device 828 enables a user with the capability to maneuver a computer cursor about the viewing area of GUI 840 and select areas or features in the viewing area of GUI 840. CPU 826 may be coupled to keyboard 830. Keyboard 830 enables a user with the capability to input alphanumeric textual information to CPU 826. CPU 826 may be coupled to microphone 832. Microphone 832 enables audio produced by a user to be recorded, processed and communicated by CPU 826. CPU 826 may be connected to printer 834. Printer 834 enables a user with the capability to print information to a sheet of paper. CPU 826 may be connected to video camera 842. Video camera 842 enables video produced or captured by user to be recorded, processed and communicated by CPU 826.

CPU 826 may also be coupled to input/output interface 844 that connects to one or more input/output devices such as such as CD-ROM, video monitors, track balls, mice, keyboards, microphones, touch-sensitive displays, transducer card readers, magnetic or paper tape readers, tablets, styluses, voice or handwriting recognizers, or other well-known input devices such as, of course, other computers.

Finally, CPU 826 optionally may be coupled to network interface 846 which enables communication with an external device such as a database or a computer or telecommunications or internet network using an external connection shown generally as communication channel 816, which may be implemented as a hardwired or wireless communications link using suitable conventional technologies. With such a connection, CPU 826 might receive information from the network, or might output information to a network in the course of performing the method steps described in the teachings of the present invention.

Figure 9:
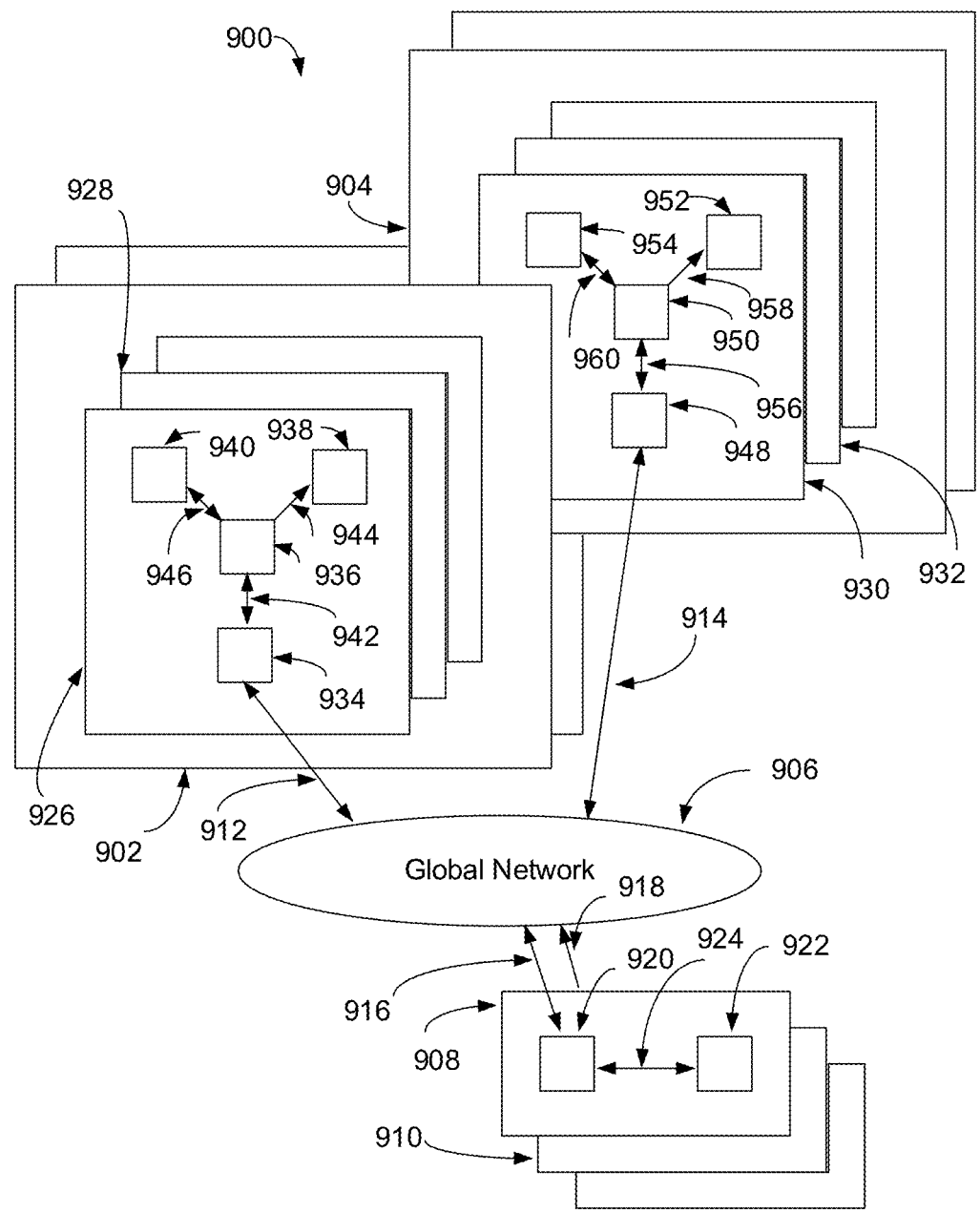
FIG. 9 illustrates a block diagram depicting a conventional client/server communication system.

FIG. 9 illustrates a block diagram depicting a conventional client/server communication system.

A communication system 900 includes a multiplicity of networked regions with a sampling of regions denoted as a network region 902 and a network region 904, a global network 906 and a multiplicity of servers with a sampling of servers denoted as a server device 908 and a server device 910.

Network region 902 and network region 904 may operate to represent a network contained within a geographical area or region. Non-limiting examples of representations for the geographical areas for the networked regions may include postal zip codes, telephone area codes, states, counties, cities and countries. Elements within network region 902 and 904 may operate to communicate with external elements within other networked regions or within elements contained within the same network region.

In some implementations, global network 906 may operate as the Internet. It will be understood by those skilled in the art that communication system 900 may take many different forms. Non-limiting examples of forms for communication system 900 include local area networks (LANs), wide area networks (WANs), wired telephone networks, cellular telephone networks or any other network supporting data communication between respective entities via hard-wired or wireless communication networks. Global network 906 may operate to transfer information between the various networked elements.

Server device 908 and server device 910 may operate to execute software instructions, store information, support database operations and communicate with other networked elements. Non-limiting examples of software and scripting languages which may be executed on server device 908 and server device 910 include C, C++, C# and Java.

Network region 902 may operate to communicate bi-directionally with global network 906 via a communication channel 912. Network region 904 may operate to communicate bi-directionally with global network 906 via a communication channel 914. Server device 908 may operate to communicate bi-directionally with global network 906 via a communication channel 916. Server device 910 may operate to communicate bi-directionally with global network 906 via a communication channel 918. Network region 902 and 904, global network 906 and server devices 908 and 910 may operate to communicate with each other and with every other networked device located within communication system 900.

Server device 908 includes a networking device 920 and a server 922. Networking device 920 may operate to communicate bi-directionally with global network 906 via communication channel 916 and with server 922 via a communication channel 924. Server 922 may operate to execute software instructions and store information.

Network region 902 includes a multiplicity of clients with a sampling denoted as a client 926 and a client 928. Client 926 includes a networking device 934, a processor 936, a GUI 938 and an interface device 940. Non-limiting examples of devices for GUI 938 include monitors, televisions, cellular telephones, smartphones and PDAs (Personal Digital Assistants). Non-limiting examples of interface device 940 include pointing device, mouse, trackball, scanner and printer. Networking device 934 may communicate bi-directionally with global network 906 via communication channel 912 and with processor 936 via a communication channel 942. GUI 938 may receive information from processor 936 via a communication channel 944 for presentation to a user for viewing. Interface device 940 may operate to send control information to processor 936 and to receive information from processor 936 via a communication channel 946. Network region 904 includes a multiplicity of clients with a sampling denoted as a client 930 and a client 932. Client 930 includes a networking device 948, a processor 950, a GUI 952 and an interface device 954. Non-limiting examples of devices for GUI 938 include monitors, televisions, cellular telephones, smartphones and PDAs (Personal Digital Assistants). Non-limiting examples of interface device 940 include pointing devices, mousse, trackballs, scanners and printers. Networking device 948 may communicate bi-directionally with global network 906 via communication channel 914 and with processor 950 via a communication channel 956. GUI 952 may receive information from processor 950 via a communication channel 958 for presentation to a user for viewing. Interface device 954 may operate to send control information to processor 950 and to receive information from processor 950 via a communication channel 960.

For example, consider the case where a user interfacing with client 926 may want to execute a networked application. A user may enter the IP (Internet Protocol) address for the networked application using interface device 940. The IP address information may be communicated to processor 936 via communication channel 946. Processor 936 may then communicate the IP address information to networking device 934 via communication channel 942. Networking device 934 may then communicate the IP address information to global network 906 via communication channel 912. Global network 906 may then communicate the IP address information to networking device 920 of server device 908 via communication channel 916. Networking device 920 may then communicate the IP address information to server 922 via communication channel 924. Server 922 may receive the IP address information and after processing the IP address information may communicate return information to networking device 920 via communication channel 924. Networking device 920 may communicate the return information to global network 906 via communication channel 916. Global network 906 may communicate the return information to networking device 934 via communication channel 912. Networking device 934 may communicate the return information to processor 936 via communication channel 942. Processor 946 may communicate the return information to GUI 938 via communication channel 944. User may then view the return information on GUI 938.

It will be further apparent to those skilled in the art that at least a portion of the novel method steps and/or system components of the present invention may be practiced and/or located in location(s) possibly outside the jurisdiction of the United States of America (USA), whereby it will be accordingly readily recognized that at least a subset of the novel method steps and/or system components in the foregoing embodiments must be practiced within the jurisdiction of the USA for the benefit of an entity therein or to achieve an object of the present invention. Thus, some alternate embodiments of the present invention may be configured to comprise a smaller subset of the foregoing means for and/or steps described that the applications designer will selectively decide, depending upon the practical considerations of the particular implementation, to carry out and/or locate within the jurisdiction of the USA. For example, any of the foregoing described method steps and/or system components which may be performed remotely over a network (e.g., without limitation, a remotely located server) may be performed and/or located outside of the jurisdiction of the USA while the remaining method steps and/or system components (e.g., without limitation, a locally located client) of the forgoing embodiments are typically required to be located/performed in the USA for practical considerations. In client-server architectures, a remotely located server typically generates and transmits required information to a US based client, for use according to the teachings of the present invention. Depending upon the needs of the particular application, it will be readily apparent to those skilled in the art, in light of the teachings of the present invention, which aspects of the present invention can or should be located locally and which can or should be located remotely. Thus, for any claims construction of the following claim limitations that are construed under 35 USC § 112 (6) it is intended that the corresponding means for and/or steps for carrying out the claimed function are the ones that are locally implemented within the jurisdiction of the USA, while the remaining aspect(s) performed or located remotely outside the USA are not intended to be construed under 35 USC § 112 (6).

It is noted that according to USA law, all claims must be set forth as a coherent, cooperating set of limitations that work in functional combination to achieve a useful result as a whole. Accordingly, for any claim having functional limitations interpreted under 35 USC § 112 (6) where the embodiment in question is implemented as a client-server system with a remote server located outside of the USA, each such recited function is intended to mean the function of combining, in a logical manner, the information of that claim limitation with at least one other limitation of the claim. For example, in client-server systems where certain information claimed under 35 USC § 112 (6) is/(are) dependent on one or more remote servers located outside the USA, it is intended that each such recited function under 35 USC § 112 (6) is to be interpreted as the function of the local system receiving the remotely generated information required by a locally implemented claim limitation, wherein the structures and or steps which enable, and breath life into the expression of such functions claimed under 35 USC § 112 (6) are the corresponding steps and/or means located within the jurisdiction of the USA that receive and deliver that information to the client (e.g., without limitation, client-side processing and transmission networks in the USA). When this application is prosecuted or patented under a jurisdiction other than the USA, then "USA" in the foregoing should be replaced with the pertinent country or countries or legal organization(s) having enforceable patent infringement jurisdiction over the present application, and "35 USC § 112 (6)" should be replaced with the closest corresponding statute in the patent laws of such pertinent country or countries or legal organization(s).

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" claim limitation implies that the broadest initial search on 112(6) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112 (6) when such corresponding structures are not explicitly disclosed in the foregoing patent specification. Therefore, for any invention element(s)/structure(s) corresponding to functional claim limitation(s), in the below claims interpreted under 35 USC § 112 (6), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112 (6) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112 (6), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing water testing device and method according to the present invention will be apparent to those skilled in the art. Various aspects of the invention have been described above by way of illustration, and the specific embodiments disclosed are not intended to limit the invention to the particular forms disclosed. The particular implementation of the water testing device and method may vary depending upon the particular context or application. By way of example, and not limitation, the water testing device and method described in the foregoing were principally directed to implementing an automated testing of water from various users using a specifically designed water testing device and a designated computer program; however, similar techniques may instead be applied to fluids other than water, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. That is, the Abstract is provided merely to introduce certain concepts and not to identify any key or essential features of the claimed subject matter. It is submitted with the understanding that it will not be used to limit or interpret the scope or meaning of the claims.

The following claims are hereby incorporated into the detailed description, with each claim standing on its own as a separate embodiment.

What is claimed is:

1. A method of testing a fluid sample comprising the steps of:
    receiving at least one instruction from a first computing system to schedule a test of a fluid;
    operating an input device for importing at least a quantity of the fluid from a source;
    filling a vial with a pre-determined amount of the imported fluid;
    operating a drawing device for drawing a pre-determined amount of a reagent;
    activating the drawing device for adding the pre-determined amount of the reagent to the vial;
    mixing the fluid and reagent in the vial;
    reading an output of a photocolorimeter, the output indicating a result of the reaction of the pre-determined amount of the imported fluid and the pre-determined amount of the reagent;
    transmitting the result of the reaction to a second computing system; and
    sending an order to another device to dose and correct for a missing chemical.

2. The method as recited in claim 1, further comprising the step of flushing the vial with a portion of the quantity of the imported fluid, before adding the reagent.

3. The method as recited in claim 1, further comprising calibrating the photocolorimeter.

4. The method as recited in claim 1, further comprising the step of activating a stirring device for mixing the pre-determined amount of the imported fluid and the pre-determined amount of the reagent.

5. The method as recited in claim 1, further comprising the step of transmitting the result of the photocolorimetric reading to a cloud server.

6. The method as recited in claim 1, wherein said reading occurs at a pre-determined time after mixing of the pre-determined amount of the imported fluid and the pre-determined amount of the reagent.

7. A computer-implemented system for testing a fluid sample, comprising:
- a fluid testing input device for testing fluids, including:
  - a system controller;
  - a vial;
  - a reagent dispenser;
  - a mixer(s), and
  - a photocolorimeter,
  - a system controller configured to implement a test schedule receiving module, a communication module, a voice input module, a visual input/output module, a test method selection module, a reagent selection module, a reagent amount determination module, a wash cycle determination module, a rest time determination module, a data analysis module, a result generating module, an interface module and a heuristic module;
- a user device configured to communicate with the fluid testing input device over a communication network;
- a server device configured to communicate with the fluid testing input device and the user device over the communication network;
- wherein the fluid testing input device adapted to:
  - receive a fluid sample into the vial from a predetermined source;
  - dispense a reagent and mix the fluid sample and the reagent;
  - test the mixed fluid sample and reagent in the photocolorimeter;
  - generate a signal in/by the photocolorimeter for transmitting to the user device;
- wherein the user device is configured to, upon receiving the signal from the photocolorimeter, generate electronic instructions including pre-determined parameters pertaining to the fluid testing device, and transmit the instructions to the server;
- wherein the server device is configured to process the instruction received from the user device and send a control signal to the fluid testing device, thereby controlling the operation of the fluid testing input device based on the instructions from the user device.

8. The system of claim 7 further configured for operating a flushing device for flushing the vial with a pre-determined amount of the imported fluid.

9. The system of claim 7 further configured for calibrating the photocolorimeter.

10. The system of claim 7 further configured to activate a stirring device for mixing the imported fluid and the reagent.

11. The system of claim 8 further configured to initiate a photocolorimetric reading according to pre-determined time and time intervals.

* * * * *